(12) United States Patent
Zielinski et al.

(10) Patent No.: US 8,241,222 B2
(45) Date of Patent: Aug. 14, 2012

(54) MONITORING HEMODYNAMIC STATUS BASED ON INTRACARDIAC OR VASCULAR IMPEDANCE

(75) Inventors: Todd M. Zielinski, Ham Lake, MN (US); Douglas A. Hettrick, Andover, MN (US); Mattias Rouw, Amhem (NL)

(73) Assignee: Medtronic, Inc., Minneapolis, MN (US)

( * ) Notice: Subject to any disclaimer, the term of this patent is extended or adjusted under 35 U.S.C. 154(b) by 896 days.

(21) Appl. No.: 12/262,941

(22) Filed: Oct. 31, 2008

(65) Prior Publication Data
US 2010/0030086 A1 Feb. 4, 2010

Related U.S. Application Data

(60) Provisional application No. 61/085,235, filed on Jul. 31, 2008.

(51) Int. Cl.
*A61B 5/02* (2006.01)

(52) U.S. Cl. ........ 600/506; 600/485; 600/521; 600/547; 607/23

(58) Field of Classification Search .......... 600/506, 600/521, 547; 607/23
See application file for complete search history.

(56) References Cited

U.S. PATENT DOCUMENTS

| | | | |
|---|---|---|---|
| 4,374,382 A | 2/1983 | Markowitz | |
| 4,674,518 A | 6/1987 | Salo | |
| 4,807,638 A | 2/1989 | Sramek | |
| 5,003,976 A * | 4/1991 | Alt | 607/18 |
| 5,117,824 A | 6/1992 | Keimel et al. | |
| 5,417,717 A | 5/1995 | Salo et al. | |
| 5,824,029 A | 10/1998 | Weijand et al. | |
| 6,360,123 B1 | 3/2002 | Kimchi et al. | |
| 6,438,408 B1 | 8/2002 | Mulligan et al. | |
| 6,623,434 B2 | 9/2003 | Chesney et al. | |
| 6,648,828 B2 | 11/2003 | Friedman et al. | |
| 6,871,089 B2 * | 3/2005 | Korzinov et al. | 600/518 |

(Continued)

FOREIGN PATENT DOCUMENTS

| | | |
|---|---|---|
| WO | WO 2005/110535 A1 | 11/2005 |
| WO | 2006/063255 A2 | 6/2006 |
| WO | WO 2006/102905 A1 | 10/2006 |

OTHER PUBLICATIONS

International Search Report and Written Opinion of related PCT Application No. PCT/US2009/052450 dated Oct. 30, 2009 (14 pages).

(Continued)

*Primary Examiner* — Melanie J Yu
*Assistant Examiner* — Erik B Crawford
(74) *Attorney, Agent, or Firm* — Michael C. Soldner

(57) ABSTRACT

This disclosure relates to monitoring intracardiac or vascular impedance to determine a change in hemodynamic status by detecting changes in an impedance parameter over cardiac cycles. An example method includes measuring a plurality of impedance values of a path within a patient over time, wherein the path includes at least one blood vessel or cardiac chamber of the patient, and wherein the impedance values vary as a function of blood pressure within the at least one vessel or chamber, determining a plurality of values of an impedance parameter over time based on the measured impedance values, wherein each of the impedance parameter values is determined based on a respective sub-plurality of the impedance values, comparing at least one of the impedance parameter values to at least one prior impedance parameter value, and identifying a change in a cardiovascular parameter related to the blood pressure based on the comparison.

5 Claims, 24 Drawing Sheets

U.S. PATENT DOCUMENTS

| | | | |
|---|---|---|---|
| 7,029,447 B2 | 4/2006 | Rantala | |
| 7,164,947 B2 | 1/2007 | Holmstrom et al. | |
| 7,181,272 B2 | 2/2007 | Struble et al. | |
| 7,283,873 B1 | 10/2007 | Park et al. | |
| 7,391,257 B1 | 6/2008 | Denison et al. | |
| 7,736,319 B2* | 6/2010 | Patangay et al. | 600/528 |
| 2002/0147475 A1 | 10/2002 | Scheiner et al. | |
| 2004/0147969 A1 | 7/2004 | Mann et al. | |
| 2005/0096557 A1* | 5/2005 | Vosburgh et al. | 600/509 |
| 2005/0192488 A1 | 9/2005 | Bryenton et al. | |
| 2006/0074404 A1* | 4/2006 | Struble | 604/890.1 |
| 2007/0021683 A1 | 1/2007 | Benditt et al. | |
| 2007/0129765 A1 | 6/2007 | Gilkerson et al. | |
| 2008/0033498 A1 | 2/2008 | Mann et al. | |
| 2008/0103399 A1* | 5/2008 | Patangay et al. | 600/508 |
| 2008/0132800 A1 | 6/2008 | Hettrick et al. | |
| 2008/0139958 A1 | 6/2008 | Uemura et al. | |

OTHER PUBLICATIONS

International Preliminary Report on Patentability, dated Feb. 10, 2011, from corresponding PCT Application No. PCT/US2009/050977, 7 pages.

International Search Report and Written Opinion, dated Oct. 30, 2009, from corresponding PCT Application No. PCT/US2009/050977, 12 pages.

International Preliminary Report on Patentability, dated Feb. 10, 2011, from PCT Application No. PCT/US2009/052450, 8 pages.

Weiss et al., "Do Changes in Transcardiac Impedance Modulation Correlate With Haemodynamic Status," *Australasian Physical & Engineering Sciences in Medicine*, vol. 15, No. 2, 1992, pp. 57-64.

Paul Steendijk et al., "Pressure-volume measurements by conductance catheter during cardiac resynchronization therapy," *European Heart Journal Supplements* (2004) 6 (Supplement D), D35-D42.

A.V. Blinov et al., "Plethysmographic Impedance Device for Measuring Blood Pressure," *Measurement Technniques*, vol. 40, No. 2, 1997 (pp. 188-192).

Klaas R. Visser et al., "Blood Pressure Esimation Investigated by Electric Impedance Measurement," *Annual International Conference of the IEEE Engineering in Medicine and Biology Society*, vol. 12, No. 2 (1990) pp. 691-692.

U.S. Appl. No. 12/263,065, filed Oct. 31, 2008 entitled Estimating Cardiovascular Pressure and Volume Using Impedance Measurements by Douglas A. Hettrick et al.

* cited by examiner

US 8,241,222 B2

MONITORING HEMODYNAMIC STATUS BASED ON INTRACARDIAC OR VASCULAR IMPEDANCE

This application claims the benefit of U.S. Provisional Application No. 61/085,235, filed Jul. 31, 2008, which is hereby incorporated by reference in its entirety.

TECHNICAL FIELD

This disclosure relates to medical devices and, more particularly, to external or implantable medical devices that monitor cardiovascular parameters.

BACKGROUND

Congestive Heart Failure (CHF) refers to a clinical syndrome of symptomatic events associated with compromised cardiac function. The term "heart failure" may describe the inability of the heart to supply sufficient blood flow to meet the physiological needs of the peripheral tissues. Heart failure may be associated with one or both of systolic dysfunction and diastolic dysfunction.

Systolic dysfunction refers to the inability of the cardiac contractile mechanism to develop adequate force, e.g., the inability to overcome mechanical afterload. The heart may compensate for reduced systolic function by dilating or stretching in order to improve ejection by increasing preload via the Frank-Starling mechanism. Thus, systolic dysfunction may often be characterized by a dilated, thin-walled ventricle with low ejection fraction.

Diastolic dysfunction refers to the inability of a ventricle to adequately fill. Diastolic dysfunction may arise from several mechanisms, including hypertension. Increased afterload due to increased systemic vascular resistance or reduced arterial compliance can lead to increased wall stress according to the Law of LaPlace. The ventricle may compensate for such increased wall stress by thickening or hypertrophying. Thus, diastolic ventricular dysfunction may often be characterized by ventricular hypertrophy and, perhaps, increased ejection fraction.

Hypertension may be a precursor to, or aggravating factor for, heart failure. Renal failure may occur as a result of heart failure, or may occur independently of heart failure, and may result in hypertension, edema, or peripheral fluid accumulation. A variety of cardiovascular pressures, e.g., intracardiac, arterial, and venous pressures, have been proposed as indicators of the progression of maladies such as heart failure, hypertension, or renal failure, as well as the hemodynamic status of patient in general. The progression of heart failure and renal failure may also be monitored based on thoracic or peripheral fluid accumulation, i.e., edema.

SUMMARY

In general, this disclosure discusses techniques for detecting changes in the cardiovascular performance, and more generally hemodynamic status, of a patient by monitoring impedance values of a cardiac chamber or blood vessel. A medical device, such as an implantable medical device (IMD), may monitor impedance values of a path that is between electrodes and traverses a cardiac chamber or a blood vessel. It has been determined that the impedance of such a path is correlated with and varies in substantially the same manner as the pressure in the chamber or vessel. Thus, the impedance of the path may be monitored as a surrogate for the pressure in the chamber or vessel, and variations in the impedance over time may indicate a change in hemodynamic performance in a manner analogous to techniques used to identify changes to hemodynamic performance based pressure.

In general, impedance values of the path may define a periodic function, e.g., waveform, the period of which may be correlated with the cardiac cycle and heart rate of the patient, in much the same manner that a cardiovascular pressure waveform defines a periodic function. The device may monitor changes in the waveform over a number of periods. For example, the device may compare a mean impedance of a first period to a mean impedance of a subsequent period. The device may also compare a range (corresponding to the difference between the waveform maximum and the waveform minimum) of a first period to a range of a subsequent period. The device may also compare a value of the first derivative of the waveform during a first period to a value of the first derivative of the waveform during a subsequent period. In any case, the device may determine whether the hemodynamic status of the patient has changed based on such comparisons between periods. Furthermore, the device may determine whether the hemodynamic status of the patient has changed based on the time duration between events during such a period, such as a time duration between an electrogram R-wave and an impedance maximum, minimum, or the like.

In this manner, a medical device may determine various conditions related to cardiovascular performance of the patient. For example, the device may determine a change in hemodynamic performance, hypertension, blood pressure, stroke volume, peripheral fluid accumulation, afterload, systolic function, or other characteristics of cardiovascular performance. In some examples, the device may also deliver a therapy to the patient, such that the device may start, stop, or modify the therapy based on the change in cardiovascular performance. In some examples, the device may be communicatively coupled to a second medical device, which may start, stop, or modify a therapy delivered to the patient based on information from the monitoring device. In some examples, the device may trigger or send an alert in response to a determined change in cardiovascular performance.

In one example, a method includes the steps of measuring a plurality of impedance values of a path within a patient over time, wherein the path includes at least one blood vessel or cardiac chamber of the patient, and wherein the impedance values vary as a function of blood pressure within the at least one vessel or chamber, determining a plurality of values of an impedance parameter over time based on the measured impedance values, wherein each of the impedance parameter values is determined based on a respective sub-plurality of the impedance values, comparing at least one of the impedance parameter values to at least one prior impedance parameter value, and identifying a change in a cardiovascular parameter related to the blood pressure based on the comparison.

In another example, a medical system includes an electrical sensing module to measure a plurality of impedance values of a path within a patient over time, wherein the path includes at least one blood vessel or cardiac chamber of the patient, and wherein the impedance values vary as a function of blood pressure within the at least one vessel or chamber, an impedance parameter module to determine a plurality of values of an impedance parameter over time based on the impedance values measured by the electrical sensing module, wherein the impedance parameter module determines each of the impedance parameter values based on a respective sub-plurality of the impedance values, a memory to store the impedance parameter values, a comparison module to compare at least one of the impedance parameter values to at least one prior impedance parameter value, wherein the comparison module is configured to identify a change in a cardiovascular parameter related to the blood pressure based on the comparison. The medical system may also include a response module to execute a response when the comparison module identifies a change in the cardiovascular parameter.

In another example, a system includes an implantable medical device configured to measure a plurality of impedance values of a path within a patient over time, wherein the path includes at least one blood vessel or cardiac chamber of the patient, and wherein the impedance values vary as a function of blood pressure within the at least one vessel or chamber, and a computing device in communication with the medical device. The computing device is configured to retrieve the impedance values from the medical device, and determine a plurality of values of an impedance parameter over time based on the impedance values retrieved from the medical device, wherein each of the impedance parameter values are based on a respective sub-plurality of the impedance values. The computing device is configured to compare at least one of the impedance parameter values to at least one prior impedance parameter value, and is further configured to identify a change in a cardiovascular parameter related to the blood pressure based on the comparison. The computing device may be, for example, a programmer in local wireless communication with the medical device. The computing device may also be a remote server. The implantable medical device may deliver therapy to the patient. The computing device may modify the therapy delivered to the patient by the implantable medical device in response to an identified change of the cardiovascular parameter.

In another example, computer-readable medium contains instructions. The computer-readable medium may be a computer readable storage medium. The instructions cause a programmable processor to measure a plurality of impedance values of a path within a patient over time, wherein the path includes at least one blood vessel or cardiac chamber of the patient, and wherein the impedance values vary as a function of blood pressure within the at least one vessel or chamber, determine a plurality of values of an impedance parameter over time based on the measured impedance values, wherein each of the impedance parameter values is determined based on a respective sub-plurality of the impedance values, compare at least one of the impedance parameter values to at least one prior impedance parameter value, identify a change in a cardiovascular parameter related to the blood pressure based on the comparison, and execute a programmed response upon identifying a change in the cardiovascular parameter.

The details of one or more examples of the invention are set forth in the accompanying drawings and the description below. Other features, objects, and advantages will be apparent from the description and drawings, and from the claims.

DETAILED DESCRIPTION

Figure 1:
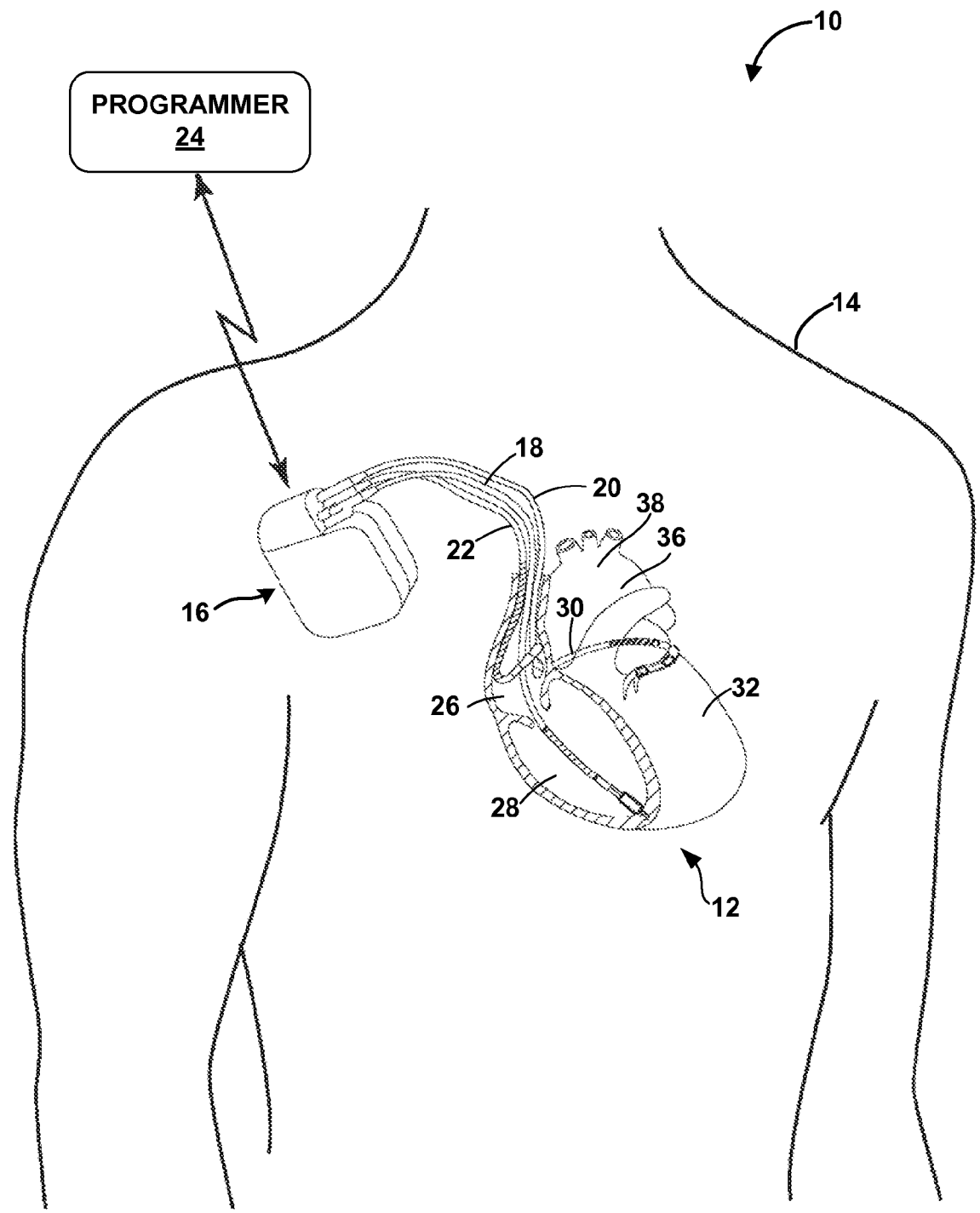
FIG. 1 is a conceptual diagram illustrating an example therapy system that may be used to provide therapy to a heart of a patient.

FIG. 1 is a conceptual diagram illustrating an example therapy system 10 that may be used to provide therapy to heart 12 of patient 14. Therapy system 10 includes IMD 16, which is coupled to leads 18, 20, and 22, and programmer 24. IMD 16 may be, for example, an implantable pacemaker, cardioverter, and/or defibrillator that provides electrical signals to heart 12 via electrodes coupled to one or more of leads 18, 20, and 22. Patient 12 is ordinarily, but not necessarily, a human patient.

Leads 18, 20, 22 extend into the heart 12 of patient 16 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar. IMD 16 may also provide defibrillation therapy and/or cardioversion therapy via electrodes located on at least one of the leads 18, 20, 22. IMD 16 may detect, for example, arrhythmia of heart 12, such as fibrillation of ventricles 28 and 32, and deliver defibrillation therapy to heart 12 in the form of electrical pulses. In some examples, IMD 16 may be programmed to deliver a progression of therapies, e.g., pulses with increasing energy levels, until a fibrillation of heart 12 is stopped. IMD 16 detects fibrillation employing one or more fibrillation detection techniques known in the art.

In some examples, programmer 24 may be a handheld computing device, computer workstation, or networked computing device. Programmer 24 may include a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, by which a user may interact with the user interface. In some examples, a display of programmer 24 may include a touch screen display, and a user may interact with programmer 24 via the display. It should be noted that the user may also interact with programmer 24 remotely via a networked computing device.

A user, such as a physician, technician, surgeon, electrophysiologist, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD.

For example, the user may use programmer 24 to retrieve information from IMD 16 regarding the rhythm of heart 12, trends therein over time, or arrhythmic episodes. As another example, the user may use programmer 24 to retrieve information from IMD 16 regarding other sensed parameters of patient 14, such as intracardiac or intravascular impedance values. As another example, the user may use programmer 24 to retrieve information from IMD 16 regarding the performance or integrity of IMD 16 or other components of system 10, such as leads 18, 20 and 22, or a power source of IMD 16. As another example, the user may interact with programmer 24 to program, e.g., select parameters for, therapies provided by IMD 16, such as pacing, cardioversion and/or defibrillation.

IMD 16 and programmer 24 may communicate via wireless communication using any techniques known in the art. In some examples, IMD 16 may include a response module that sends an alert to, e.g., programmer 24 when IMD 16 detects a problem with heart 12 or other organs or systems of patient 14. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

IMD 16 is an example of a medical device that may monitor impedance values of a path that is between electrodes and traverses a cardiac chamber or a blood vessel according to the techniques described in this disclosure. The electrodes may be located on leads 18, 20 and 22 and, in some examples, may include an electrode on a housing of IMD 16. The electrodes are endpoints of a path through, e.g., a cardiac chamber or blood vessel. In some examples, therapy system 10 may include an additional or alternative lead or lead segment (not shown in FIG. 1) that deploys one or more electrodes within the vena cava or other vein, or within or near the aorta. These electrodes may allow alternative electrode configurations that may provide improved impedance determination for some chambers or vessels, for some applications, or for some patients.

Figure 2:
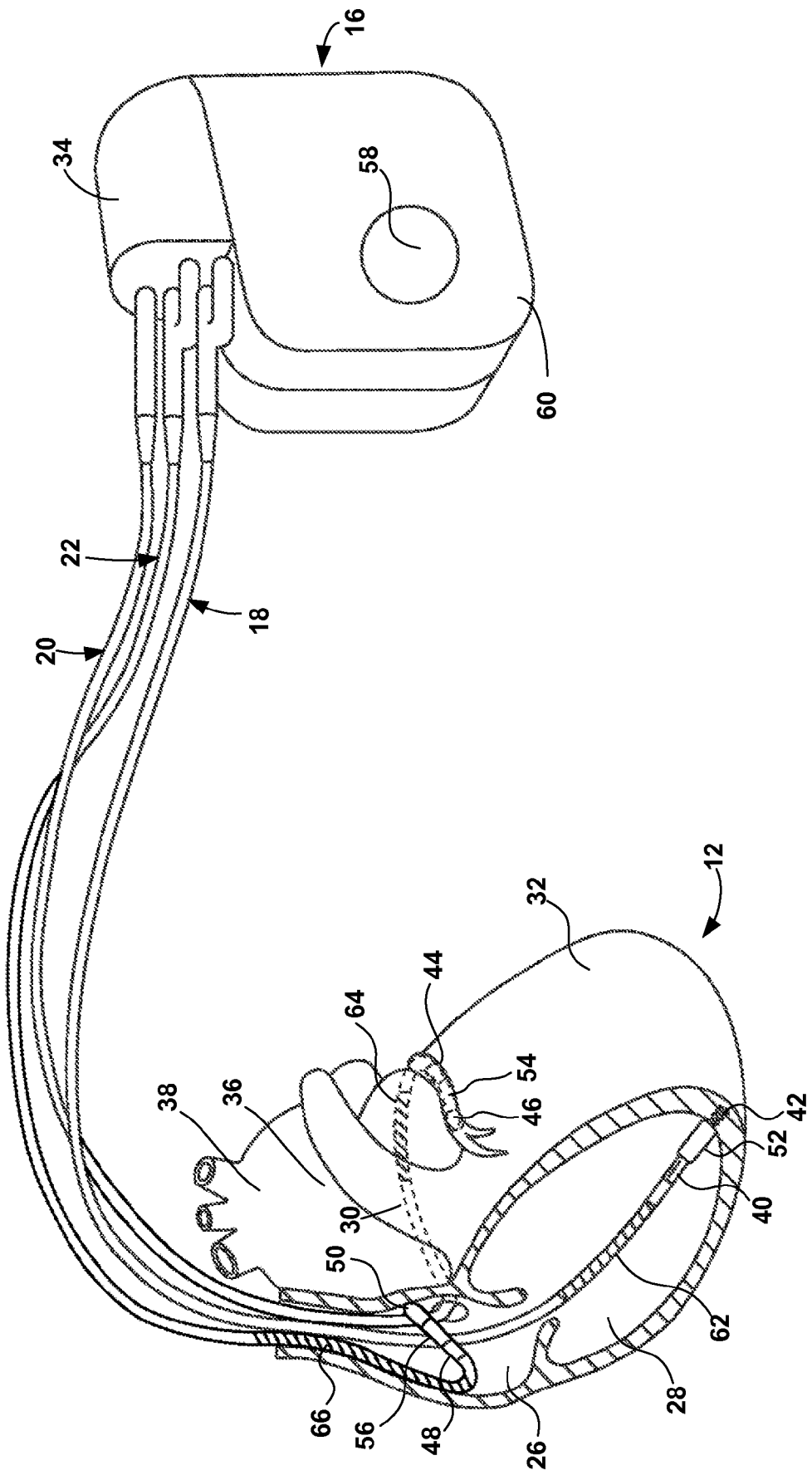
FIG. 2 is a conceptual diagram illustrating an example implantable medical device (IMD) and corresponding leads in greater detail.

FIG. 2 is a conceptual diagram illustrating IMD 16 and leads 18, 20, 22 of therapy system 10 in greater detail. Leads 18, 20, 22 may be electrically coupled to a stimulation generator and a sensing module of IMD 16 via connector block 34. In some examples, proximal ends of leads 18, 20, 22 may include electrical contacts that electrically couple to respective electrical contacts within connector block 34 of IMD 16. In addition, in some examples, leads 18, 20, 22 may be mechanically coupled to connector block 34 with the aid of set screws, connection pins, snap connectors, or another suitable mechanical coupling mechanism.

Each of the leads 18, 20, 22 includes an elongated insulative lead body, which may carry a number of concentric coiled conductors separated from one another by tubular insulative sheaths. Bipolar electrodes 40 and 42 are located adjacent to a distal end of lead 18 in right ventricle 28. In addition, bipolar electrodes 44 and 46 are located adjacent to a distal end of lead 20 in coronary sinus 30 and bipolar electrodes 48 and 50 are located adjacent to a distal end of lead 22 in right atrium 26. There are no electrodes located in left atrium 36, but other examples may include electrodes in left atrium 36. Furthermore, other examples may include electrodes in other locations, such as the aorta or a vena cava, or epicardial or extracardial electrodes proximate to any of the chambers or vessels described herein.

Electrodes 40, 44, and 48 may take the form of ring electrodes, and electrodes 42, 46, and 50 may take the form of extendable helix tip electrodes mounted retractably within insulative electrode heads 52, 54, and 56, respectively. In other examples, one or more of electrodes 42, 46, and 50 may take the form of small circular electrodes at the tip of a tined lead or other fixation element. Leads 18, 20, 22 also include elongated electrodes 62, 64, 66, respectively, which may take the form of a coil. Each of the electrodes 40, 42, 44, 46, 48, 50, 62, 64, and 66 may be electrically coupled to a respective one of the coiled conductors within the lead body of its associated lead 18, 20, 22, and thereby coupled to respective ones of the electrical contacts on the proximal end of leads 18, 20, 22.

In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. As described in further detail with reference to FIG. 4, housing 60 may enclose a signal generator that generates therapeutic stimulation, such as cardiac pacing pulses and defibrillation shocks, as well as a sensing module for monitoring the rhythm of heart 12.

IMD 16 may sense electrical signals attendant to the depolarization and repolarization of heart 12 via electrodes 40, 42, 44, 46, 48, 50, 58, 62, 64, and 66. The electrical signals are conducted to IMD 16 from the electrodes via the respective leads 18, 20, 22 or, in the case of housing electrode 58, a conductor couple to housing electrode 58. IMD 16 may sense such electrical signals via any bipolar combination of electrodes 40, 42, 44, 46, 48, 50, 58, 62, 64, and 66. Furthermore, any of the electrodes 40, 42, 44, 46, 48, 50, 58, 62, 64, and 66 may be used for unipolar sensing in combination with housing electrode 58.

In some examples, IMD 16 delivers pacing pulses via bipolar combinations of electrodes 40, 42, 44, 46, 48 and 50 to produce depolarization of cardiac tissue of heart 12. In some examples, IMD 16 delivers pacing pulses via any of electrodes 40, 42, 44, 46, 48 and 50 in combination with housing electrode 58 in a unipolar configuration. Furthermore, IMD 16 may deliver defibrillation pulses to heart 12 via any combination of elongated electrodes 62, 64, 66, and housing electrode 58. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy or other materials known to be usable in implantable defibrillation electrodes.

Any combination of electrodes 40, 42, 44, 46, 48, 50, 60, 62, 64 and 66 may be used for measuring impedance in accordance with the techniques of this disclosure. In some examples a single pair of electrodes may be selected to generate an electrical field and to measure the impedance of the resulting current. For example, electrodes 42 and 46 may be used to generate an electrical field and to measure impedance values across left ventricle 32. In other examples, a first pair of electrodes may be selected to generate an electrical field and a second pair of electrodes may be selected to measure the impedance of the resulting current. For example, electrodes 42 and 46 may be used to generate a first electrical field, and electrodes 40 and 44 may be used to measure the impedance of the resulting current.

In further examples, multiple pairs of electrodes may be selected to generate multiple electrical fields. The electrodes may be selected such that the multiple electrical fields are substantially homogenous or uniform over the cardiovascular region of interest. For example, electrodes 42 and 46 may be used to generate a first electrical field, electrodes 62 and 64 may be used to generate a second electrical field, and electrodes 40 and 44 may be used to measure the impedance of the resulting current. The combined electrical field may be substantially homogeneous over portions of interest in left ventricle 32, thereby resulting in a more accurate estimation than if only a single pair of electrodes were used to generate a single electric field. In some examples, elongated electrodes 62, 64 and 66 may be used to generate uniform electric fields across a large region of interest.

In additional examples, multiple pairs of measurement electrodes may be selected to filter out "noise" resulting from the electrical fields traveling through regions that are not of interest. For example, electrodes 42 and 46 may generate a first electrical field across portions of right ventricle 28 and left ventricle 32 and a first impedance may be measured by electrodes 40 and 44. In addition, electrodes 42 and 62 may generate a second electrical field across portions of right ventricle 28 and a second impedance may be measured by electrodes 42 and 62. The first and second impedances may be subtracted or otherwise processed to determine the impedance associated with left ventricle 32. In this manner, multiple measurement electrodes may be used to filter out "noise" within a measured signal and thereby provide a more robust determination of impedance values of a path.

The configuration of therapy system 10 illustrated in FIGS. 1 and 2 is merely one example. It should be understood that various other electrode and lead configurations for measuring impedance are within the scope of this disclosure. For example, a therapy system may include epicardial leads and/or patch electrodes instead of or in addition to transvenous leads 18, 20, 22 illustrated in FIG. 1. Further, IMD 16 need not be implanted within patient 14. For examples in which IMD 16 is not implanted in patient 14, IMD 16 may deliver defibrillation pulses and other therapies to heart 12 via percutaneous leads that extend through the skin of patient 14 to a variety of positions within or outside of heart 12.

Figure 3:
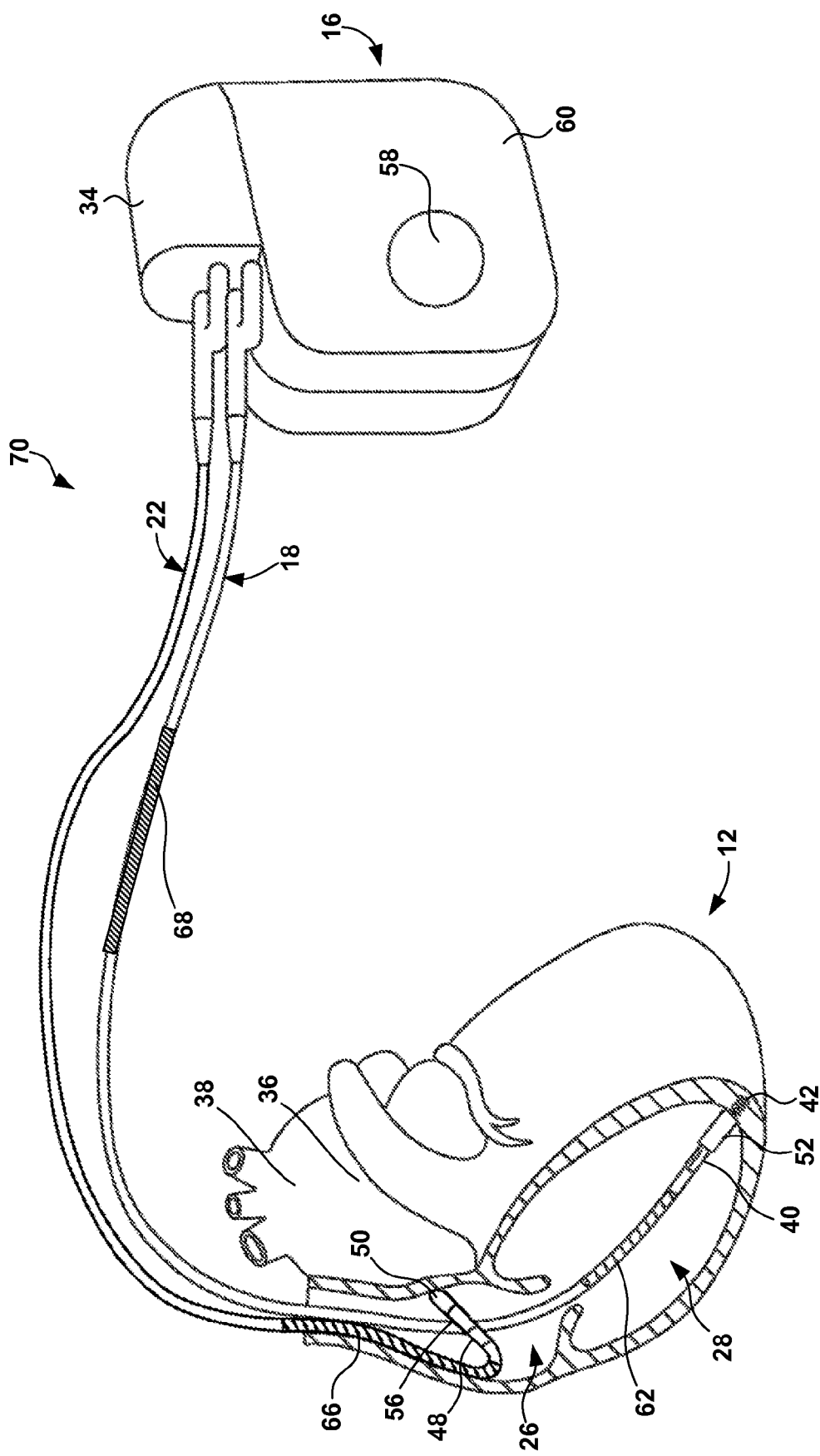
FIG. 3 is a conceptual diagram illustrating another example of a therapy system, which is similar to the therapy system of FIGS. 1-2, but includes two leads rather than three leads.

In addition, in other examples, a therapy system may include any suitable number of leads coupled to IMD 16, and each of the leads may extend to any location within or proximate to heart 12. For example, other examples of therapy systems may include three transvenous leads located as illustrated in FIGS. 1 and 2, and an additional lead located within or proximate to left atrium 36. As another example, other examples of therapy systems may include a single lead that extends from IMD 16 into right atrium 26 or right ventricle 28, or two leads that extend into a respective one of the right ventricle 26 and right atrium 26. An example of this type of therapy system is shown in FIG. 3. Any electrodes located on these additional leads may be used to measure impedance values according to techniques described herein.

FIG. 3 is a conceptual diagram illustrating another example of therapy system 70, which is similar to therapy system 10 of FIGS. 1-2, but includes two leads 18, 22, rather than three leads. Leads 18, 22 are implanted within right ventricle 28 and right atrium 26, respectively. Additionally, lead 18 includes electrode 68, which may take the form of a coil, as in the example of FIG. 3. In this manner, electrodes 68 and 66, for example, may be used to generate an electrical field and to measure impedance values across aorta 38. Therapy system 70 shown in FIG. 3 may also be useful for providing defibrillation and pacing pulses to heart 12. System 70 may also determine impedance values in accordance with the techniques described herein. Moreover, system 70 may determine changes in the impedance values over time to determine changes in cardiovascular performance and, more generally, hemodynamic status, as discussed herein.

Figure 4A:
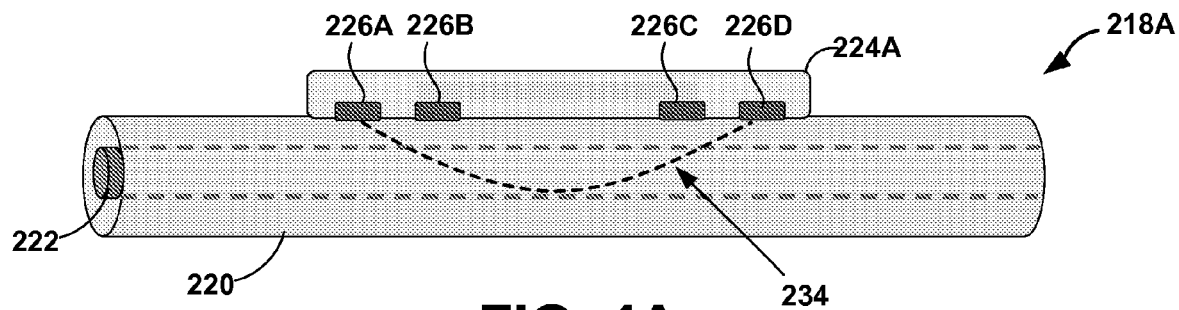
FIG. 4A-4C are conceptual diagrams illustrating example systems implanted in a patient's body near a blood vessel, such as the femoral artery.
Figure 4B:
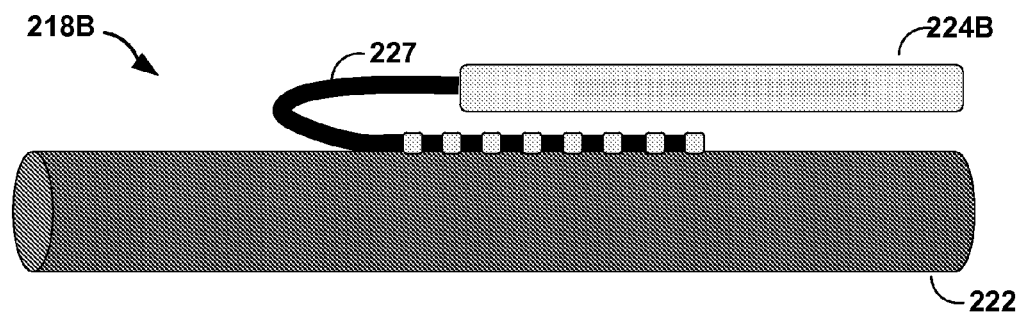
Figure 4C:
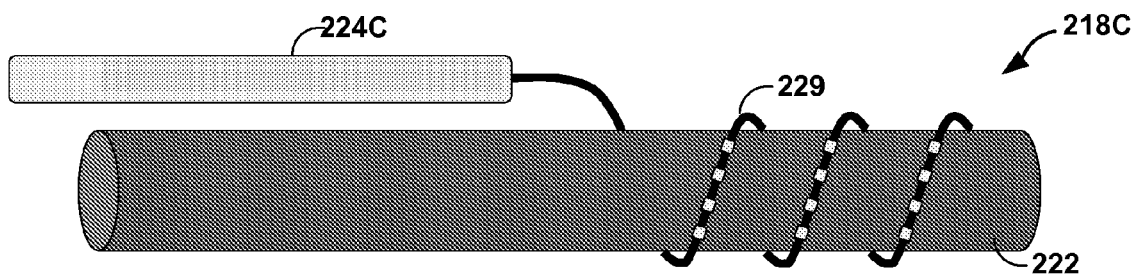

FIGS. 4A-4C are conceptual diagrams illustrating other example therapy systems 218A-218C, respectively. Therapy systems 218A-218C (collectively, "therapy systems 218") each include an IMD 224A-224C (collectively "IMDs 224"), respectively. Although not illustrated in FIGS. 4A-4C, each of systems 218 may include a programmer, which may be substantially similar to programmer 24 (FIG. 1), capable of wireless communication with the IMD 224.

In the example illustrated by FIG. 4A, IMD 224A includes electrodes 226A-226D (collectively "electrodes 226") formed on a housing of IMD 224A. In other examples, an IMD 224 may include any number of electrodes on its housing, and/or may be coupled to one or more electrodes by one or more leads. For example, FIGS. 4B and 4C illustrate IMDs 224B and 224C coupled to leads 227 and 229, respectively, each of which includes a plurality of electrodes.

As illustrated in FIG. 4A, IMD 224A may be implanted subcutaneously within a thigh of a patient, such as patient 14, proximate to femoral artery 222. In the example of FIG. 4A, at least some muscle and/or fascia 220 separates IMD 224A and electrodes 226 from artery 222. In other examples, such as those illustrated by FIGS. 4B and 4C, electrodes may be more proximate and/or in contact with artery 222. As illustrated in FIGS. 4B and 4C, lead 227 may be placed laterally along artery 222, while lead 229 may be wrapped around artery 222.

In general, IMDs 224 determine impedance values of a blood vessel, such as femoral artery 222. Although the examples of FIGS. 4A-4C depict IMDs 224 as being subcutaneously implanted in the thigh proximate to femoral artery 222, IMDs 224 may be implanted (e.g., subcutaneously, thoracically, abdominally, or otherwise) proximate to any blood vessel of patient 14. Electrodes 226, as well as the electrodes of leads 227 and 229, may be placed so as to enable an electrical field to pass through femoral artery 222, or other vessel, of the patient.

For example, IMD 224A may determine impedance values of a path 234 between electrodes 226A and 226D to identify the impedance of femoral artery 222. In general, IMDs 224 may determine impedance values of any path between two or more electrodes that are electrically coupled to the IMD. Furthermore, additional electrodes may be used, as discussed with respect to FIGS. 2 and 3, to reduce noise and to isolate the impedance of the artery or other vessel. In the manner discussed herein, IMDs 224, an external programmer, or another external computing device may determine impedance parameter values based on the impedance values determined by an IMD 224, and may evaluate hemodynamic status, generate alerts, or take other actions based on the impedance parameter values.

Figure 5:
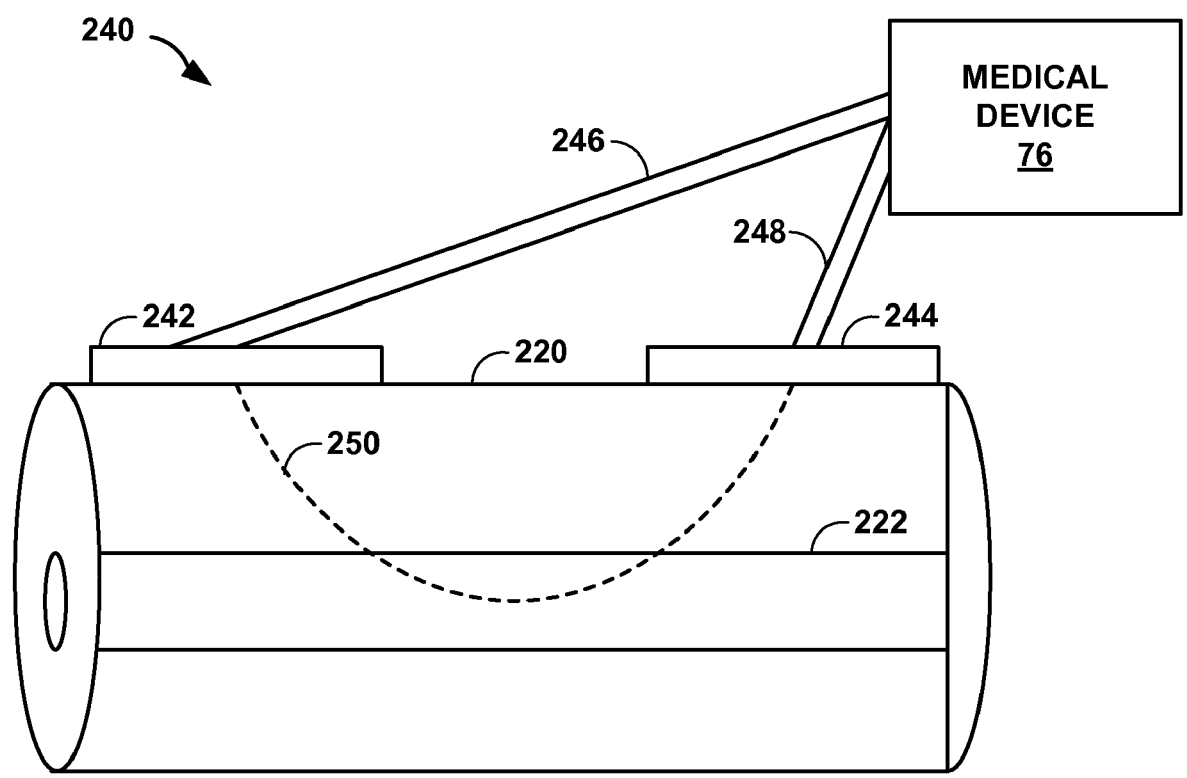
FIG. 5 is a conceptual diagram illustrating an example system with electrodes attached to the surface of a patient's body near a blood vessel, such as the femoral artery.

FIG. 5 is a conceptual diagram illustrating another example therapy system 240. Therapy system 240 also determines impedance values of a blood vessel, such as femoral artery 222 of a patient, such as patient 14. However, electrodes 242, 244 of therapy system 240 may be placed on the surface of thigh 220. Thus, therapy system 240 may transcutaneously determine impedance values of a blood vessel.

An external medical device 76 may be connected to electrodes 242, 244 through leads 246, 248, respectively. Medical device 76 of FIG. 5 may perform the functions of programmer 24 and additionally perform the techniques described herein for determining impedance values along path 250 through femoral artery 222, determining impedance parameter values from the impedance values, and comparing the impedance parameter values to identify a change in a cardiovascular parameter. When medical device 76 identifies a change in the cardiovascular parameter, medical device 76 may raise an alert or modify a therapy provided by therapy system 240. In other examples, medical device 76 may communicate with a separate external programmer that may provide any functionality ascribed to a programmer herein.

Figure 6:
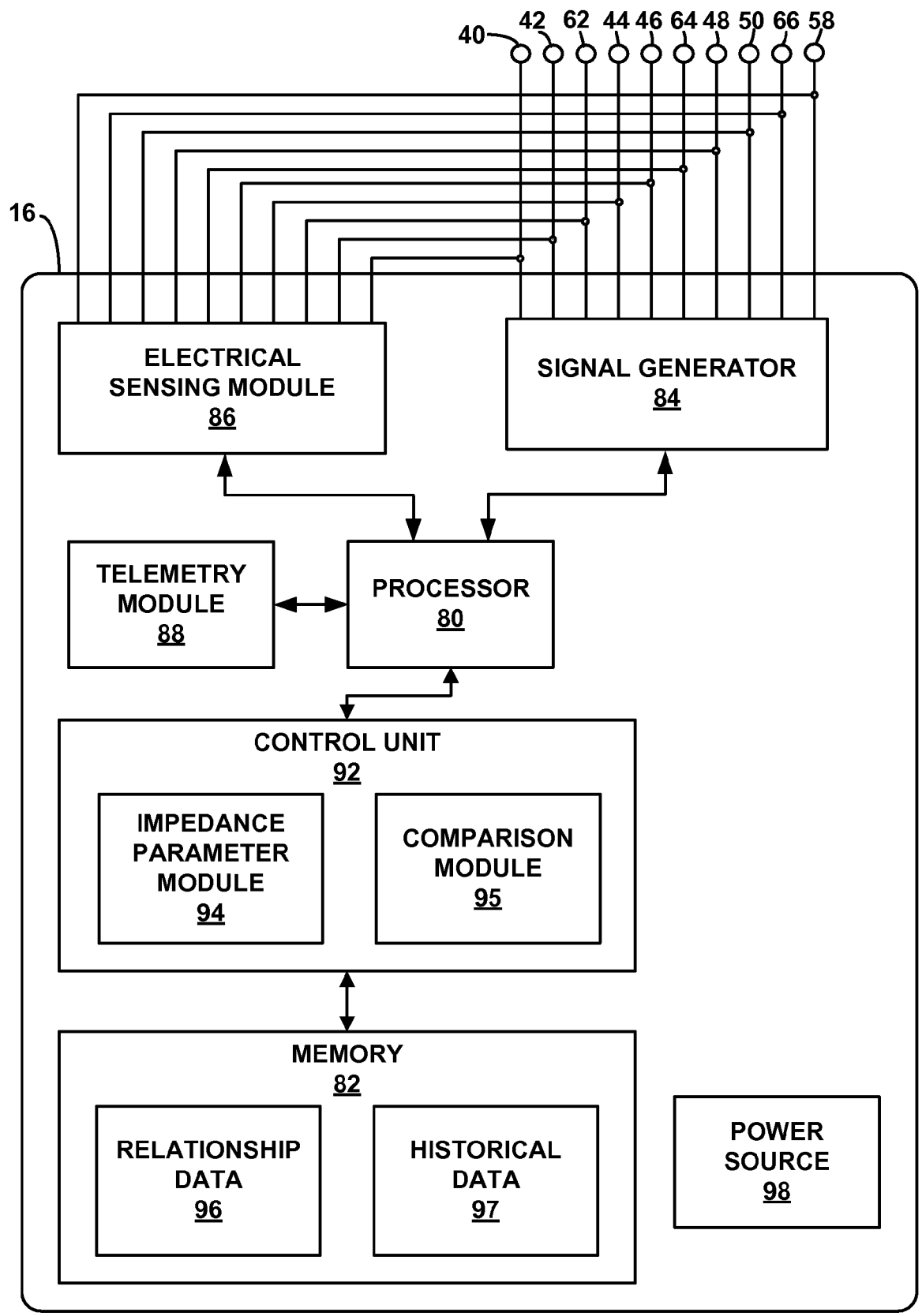
FIG. 6 is a block diagram illustrating one example configuration of an IMD.

FIG. 6 is a block diagram illustrating one example configuration of IMD 16. IMDs 224 and medical device 76 may be similarly configured. In the example illustrated by FIG. 6, IMD 16 includes a processor 80, memory 82, signal generator 84, electrical sensing module 86, telemetry module 88, and power source 98. IMD 16 further includes control unit 92, which itself includes impedance parameter module 94 and comparison module 95. Memory 82 may include computer-readable instructions that, when executed by processor 80, cause IMD 16 and processor 80 to perform various functions attributed to IMD 16, processor 80, or control unit 92 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 80 and/or control unit 92 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 and/or control unit 92 may include multiple components, such as any combination of one or more microprocessors, one or more controllers, one or more DSPs, one or more ASICs, or one or more FPGAs, as well as other discrete or integrated logic circuitry. The functions attributed to processor 80 and/or control unit 92 herein may be embodied as software, firmware, hardware or any combination thereof. In one example, control unit 92, impedance parameter module

94, and comparison module 95 may be stored as instructions in memory 82 that are executed by processor 80.

Processor 80 controls stimulation generator 84 to deliver stimulation therapy to heart 12 according to a selected one or more therapy programs, which may be stored in memory 82. Control unit 92, in the example of FIG. 6, is capable of identifying changes in impedance values to determine a change in cardiovascular performance, in accordance with the techniques described herein. In particular, impedance parameter module 94 determines values for impedance parameters based on a plurality of measured impedance values from electrical sensing module 86, and comparison module 95 compares the impedance parameter values to identify a change thereof that indicates a change in hemodynamic status. To facilitate the determination of a change in hemodynamic status, processor 80 is also capable of controlling electrode configurations and controlling the measurement of impedance values across various combinations of electrodes.

Signal generator 84 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of IMD 16. Signal generator 84 is configured to generate and deliver electrical stimulation therapy to heart 12. Signal generator 84 may therefore be considered a response module, as signal generator 84 delivers therapy in response to a determined need for therapy. For example, signal generator 84 may deliver defibrillation shocks to heart 12 via at least two electrodes 58, 62, 64, 66. Signal generator 84 may deliver pacing pulses via ring electrodes 40, 44, 48 coupled to leads 18, 20, and 22, respectively, and/or helical electrodes 42, 46, and 50 of leads 18, 20, and 22, respectively. In some examples, signal generator 84 delivers pacing, cardioversion, or defibrillation stimulation in the form of electrical pulses. In other examples, signal generator 84 may deliver one or more of these types of stimulation in the form of other signals, such as sine waves, square waves, or other substantially continuous time signals. According to the techniques in this disclosure, signal generator 84 may deliver signals to generate one or more electrical fields between at least two electrodes for impedance measurements.

Stimulation generator 84 may include a switch module and processor 80 may use the switch module to select, e.g., via a data/address bus, which of the available electrodes are used to deliver defibrillation pulses or pacing pulses. Processor 80 may also control which of electrodes 40, 42, 44, 46, 48, 50, 58, 62, 64 and 66 is coupled to signal generator 84 for impedance measurements, e.g., via the switch module. The switch module may include a switch array, switch matrix, multiplexer, or any other type of switching device suitable to selectively couple a signal to selected electrodes.

Electrical sensing module 86 monitors signals from at least one of electrodes 40, 42, 44, 46, 48, 50, 58, 62, 64 or 66 in order to monitor electrical activity of heart 12. Electrical sensing module 86 may also include a switch module to select which of the available electrodes are used to sense the heart activity. In some examples, processor 80 may select the electrodes that function as sense electrodes, or the sensing configuration, via the switch module within electrical sensing module 86, e.g., by providing signals via a data/address bus. Electrical sensing module 86 includes multiple detection channels, each of which may comprise an amplifier. In some examples, electrical sensing module 86 or processor 80 may include an analog-to-digital converter for digitizing the signal received from a sensing channel for processing by processor 80. In response to the signals from processor 80, the switch module of electrical sensing module 86 may couple the outputs from the selected electrodes to one of the detection channels. In one example, electrical sensing module 86 may measure impedance values by application of an electrical field within the cardiovascular system. Processor 80 may control which of electrodes 40, 42, 44, 46, 48, 50, 58, 62, 64 and 66 is coupled to sensing module 86 for impedance measurements, e.g., via the switching module.

Control unit 92 may generally control impedance parameter module 94 and comparison module 95. Control unit 92 may also receive instructions from processor 80. Control unit 92 may also read and store data to memory 82. In general, processor 80 may receive a plurality of values that indicates the impedance of a path from electrical sensing module 86. Impedance parameter module 94 may determine an impedance parameter value based on the impedance values. Control unit 92 may store the impedance parameter value in historical data 97 of memory 82. In one example, control unit 92 may store a plurality of impedance parameter values in historical data 97. In one example, control unit 92 may additionally store identifying information for the impedance parameter value. For example, in one example, processor 80 may determine a cardiac cycle corresponding to each of the measured impedance values from electrical sensing module 86. A new cardiac cycle may begin, for example, at a systole, diastole, an R-wave, a P-wave, or some other mechanical or electrical event of the heart of the patient. Identifying information may include, for example, a sequence number that enumerates each cardiac cycle.

Impedance parameter module 94 may determine an impedance parameter value for the impedance values. For example, impedance parameter module 94 may determine an average or mean value of the impedance values obtained over a cardiac cycle. As another example, impedance parameter module 94 may determine an amplitude for impedance values obtained over a cardiac cycle. As another example, impedance parameter module 94 may determine a range between a maximum impedance value and a minimum impedance value for a cardiac cycle. As another example, impedance parameter module 94 may determine a function for impedance values obtained over a cardiac cycle, and impedance parameter module 94 may further determine the derivative of the function, and identify a maximum of the derivative for the cardiac cycle. In other examples, impedance parameter module 94 may determine values for other impedance parameters. Impedance parameter module 94 may also determine respective values for each of a plurality of different impedance parameters, e.g. a mean and a range, or a mean, a derivative, and an amplitude, or some other combination of impedance parameter values, for each cardiac cycle. Impedance parameter module 94 may store each of the determined impedance parameter values in historical data 97.

Comparison module 95 may compare impedance parameter values determined by impedance parameter module 94. Comparison module 95 may retrieve two or more impedance parameter values from historical data 97 to compare the two or more impedance parameter values. In one example, comparison module 95 may compare two mean values from two different cardiac cycles. In another example, comparison module 95 may compare two amplitude values from two different cardiac cycles. In another example, comparison module 95 may compare two range values from two different cardiac cycles. In another example, comparison module 95 may compare two maximum derivative values from two different cardiac cycles.

Comparison module 95 may also determine whether the comparison between the two impedance parameter values represents a change in cardiovascular performance. In one example, comparison module 95 may determine whether there has been a change in a cardiovascular parameter. To make such a determination, comparison module 95 may, as examples, determine the difference or ratio between the two impedance parameter values. In one example, comparison module 95 may retrieve data from relationship data 96.

Relationship data 96 may include, for example, a relationship between the impedance parameter type under comparison by comparison module 95 and possible meanings thereof. For example, a difference in amplitudes between two cardiac cycles may indicate a change in blood pressure. A difference in the first derivative maximums between two cardiac cycles may indicate a change in stroke volume, which may be indicative of heart failure. A difference in the mean impedance values between two cardiac cycles may indicate peripheral fluid accumulation secondary to renal or heart failure. Relationship data 96 may store these or other relationships. In one example, relationship data 96 may store a threshold change or ratio to indicate an amount by which the comparison of impedance parameter values should differ for the associated condition.

In one example, relationship data 96 may store relationships between impedance parameter values in terms of increases or decreases. For example, relationship data 96 may include data indicating that a decrease in mean impedance values indicates a volume overload. As another example, relationship data 96 may include data indicating that an increase in a range between the maximum and minimum impedance values for a cardiac cycle indicates a possible increase in blood pressure. As another example, relationship data 96 may include data indicating that a decrease in the first derivative maximum indicates a decrease in systolic function.

Processor 80 controls the selection of electrode configurations and the measurement of impedances for estimating a pressure or volume for a cardiovascular chamber of interest. Processor 80 may communicate with signal generator 84 to select two or more stimulation electrodes in order to generate one or more electrical fields across a cardiovascular region of interest. Processor 80 may also communicate with electrical sensing module 86 to select two or more measurement electrodes based upon the region of interest to be measured. As discussed above, the signal and sensing electrodes may be the same electrodes.

Processor 80 may select multiple pairs of electrodes for signal delivery and measurement depending upon the estimation algorithm. For example, processor 80 may select two or more signal delivery electrodes proximate to a cardiovascular region of interest such that the resulting electrical field is substantially confined to the region of interest. As another example, processor 80 may select multiple pairs of signal delivery electrodes for generating multiple electrical fields such that the composite electrical field is substantially homogenous over the region of interest. In a further example processor 80 may select multiple pairs of measurement electrodes to cancel out measurement "noise" associated with other regions that are not part of the region of interest.

Although the example of IMD 16 of FIG. 6 includes comparison module 95, in an alternative example, comparison may be performed by another device external to IMD 16. For example, in one alternative example, programmer 24 may include a comparison module to perform the comparison of two or more impedance parameter values. Programmer 24 may retrieve the impedance parameter values from IMD 16 through, e.g., telemetry module 88. Programmer 24 may then perform the comparison to determine whether the impedance parameter values indicate a change in cardiac performance. Furthermore, in some examples, programmer 24 may include impedance parameter module 94, and determine impedance parameter values based on values that indicate impedance measured by IMD 16.

Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and the control signals for the telemetry circuit within telemetry module 88, e.g., via an address/data bus. In some examples, telemetry module 88 may provide received data to processor 80 via a multiplexer (not shown).

In some examples, processor 80 may transmit atrial and ventricular heart signals (e.g., electrogram signals) produced by atrial and ventricular sense amplifier circuits within electrical sensing module 86 to programmer 24. Programmer 24 may interrogate IMD 16 to receive the electrograms. Processor 80 may store electrograms within memory 82, and retrieve stored electrograms from memory 82. Processor 80 may also generate and store marker codes indicative of different cardiac events that electrical sensing module 86 detects, such as ventricular and atrial depolarizations, and transmit the marker codes to programmer 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety. Telemetry module 88 may also send alerts to programmer 24 when comparison module 95 identifies a possible problem in patient 14, for example. Telemetry module 88 may therefore be considered a response module, because telemetry module 88 may act in response to a detection of a problem in patient 14.

The various components of IMD 16 are coupled to power source 90, which may include a rechargeable or non-rechargeable battery. A non-rechargeable battery may be capable of holding a charge for several years, while a rechargeable battery may be inductively charged from an external device, e.g., on a daily or weekly basis.

Figure 7:
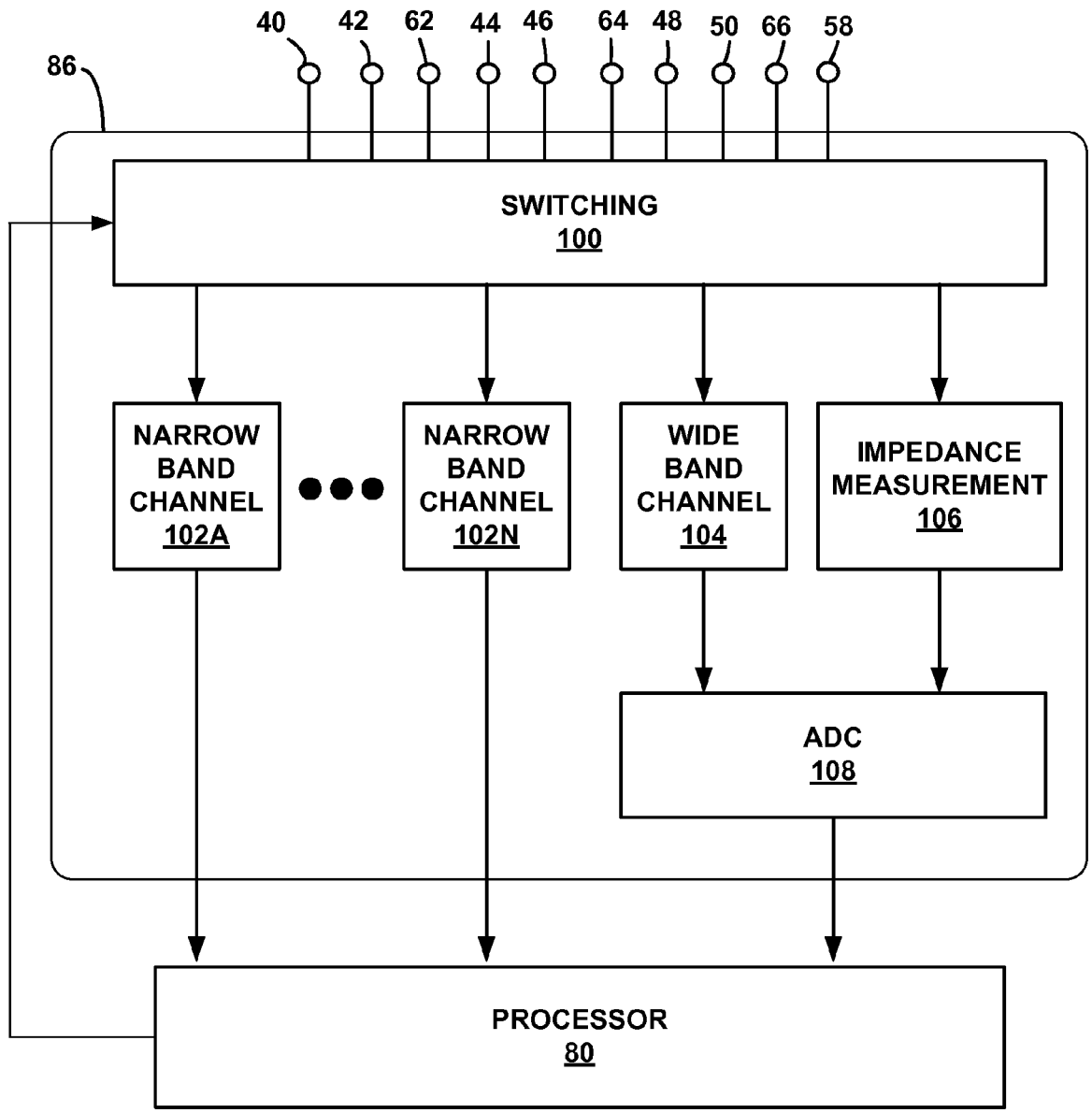
FIG. 7 is a block diagram of an example configuration of an electrical sensing module.

FIG. 7 is a block diagram of an example configuration of electrical sensing module 86. As shown in FIG. 7, electrical sensing module 86 includes multiple components including switching module 100, narrow band channels 102A to 102N, wide band channel 104, impedance measurement module 106, and analog to digital converter (ADC) 108. Switching module 100 may, based on control signals from processor 80, control which of electrodes 40, 42, 44, 46, 48, 50, 58, 62, 64 and 66 is coupled to which of channels 102 and 104 and impedance measurement module 106, at any given time.

Each of narrow band channels 102 may comprise a narrow band filtered sense-amplifier that compares the detected signal to a threshold. If the filtered and amplified signal is greater than the threshold, the narrow band channel indicates that a certain electrical heart event has occurred. Processor 80 then uses that detection in measuring frequencies of the detected events. Narrow band channels 102 may have distinct functions. For example, some various narrow band channels may be used to detect either atrial or ventricular events.

In one example, at least one narrow band channel 102 may include an R-wave amplifier that receives signals from the sensing configuration of electrodes 40 and 42, which are used for sensing and/or pacing in right ventricle 28 of heart 12. Another narrow band channel 102 may include another R-wave amplifier that receives signals from the sensing configuration of electrodes 44 and 46, which are used for sensing and/or pacing proximate to left ventricle 32 of heart 12. In some examples, the R-wave amplifiers may take the form of an automatic gain controlled amplifier that provides an adjustable sensing threshold as a function of the measured R-wave amplitude of the heart rhythm.

In addition, in some examples, a narrow band channel 102 may include a P-wave amplifier that receives signals from electrodes 48 and 50, which are used for pacing and sensing in right atrium 26 of heart 12. In some examples, the P-wave amplifier may take the form of an automatic gain controlled amplifier that provides an adjustable sensing threshold as a function of the measured P-wave amplitude of the heart rhythm. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Other amplifiers may also be used. Furthermore, in some examples, one or more of the sensing channels of sensing module 86 may be selectively coupled to housing electrode 58, or elongated electrodes 62, 64, or 66, with or instead of one or more of electrodes 40, 42, 44, 46, 48 or 50, e.g., for unipolar sensing of R-waves or P-waves in any of chambers 26, 28, or 32 of heart 12.

Wide band channel 104 may comprise an amplifier with a relatively wider pass band than the R-wave or P-wave amplifiers. Signals from the selected sensing electrodes that are selected for coupling to this wide-band amplifier may be converted to multi-bit digital signals by ADC 108. In some examples, processor 80 may store signals the digitized versions of signals from wide band channel 104 in memory 82 as EGMs. In some examples, the storage of such EGMs in memory 82 may be under the control of a direct memory access circuit.

In some examples, processor 80 may employ digital signal analysis techniques to characterize the digitized signals from wide band channel 104 to, for example detect and classify the patient's heart rhythm. Processor 80 may detect and classify the patient's heart rhythm by employing any of the numerous signal processing methodologies known in the art. Further, in some examples, processor 80 may analyze the morphology of the digitized signals from wide band channel 104 to distinguish between noise and cardiac depolarizations.

Additionally, in some examples, processor 80 and/or impedance parameter module 94 (FIG. 6) may analyze the timing and/or morphology of the digitized signals, or the timing of indications from narrow-band channels 102, to identify cardiac cycles and associate measured impedance values with cardiac cycles for the purpose of determining respective impedance parameter values for cardiac cycles. In some examples, as described below, processor 80 and/or impedance parameter module 94 may determine an interval between a cardiac electrical event, which may be indicated by an analysis of the digitized EGM signal or a signal from a narrow-band channel 102, and a fiduciary point within an impedance waveform for a cardiac cycle. This interval is another example of an impedance parameter value that may be stored, and compared or trended, over time to indicate cardiac performance.

Sensing module 86 and/or processor 80 are capable of collecting, measuring, and/or calculating impedance data utilizing any two or more of electrodes 40, 42, 44, 46, 48, 50, 58, 62, 64 and 66. In some examples, impedance measurement module 106 may measure electrical parameter values during delivery of an electrical signal between at least two of the electrodes. Processor 80 may control signal generator 84 to deliver the electrical signal between the electrodes. Processor 80 may determine impedance values based on parameter values measured by impedance measurement module 106, and store measured impedance values in memory 82. In other examples, processor 80 may pass measured impedance values to control unit 92.

In some examples, processor 80 may perform an impedance measurement by controlling delivery, from signal generator 84, of a voltage pulse between first and second electrodes. The voltage pulse may generate an electrical field between the first and second electrodes. Measurement module 106 may measure a resulting current, and processor 80 may calculate impedance values based upon the voltage amplitude of the pulse and the measured amplitude of the resulting current. In other examples, processor 80 may perform an impedance measurement by controlling delivery, from signal generator 84, of a current pulse between first and second electrodes. The current pulse may generate an electrical field between the first and second electrodes. Measurement module 106 may measure a resulting voltage, and processor 80 may calculate impedance values based upon the current amplitude of the pulse and the measured amplitude of the resulting voltage. Measurement module 106 may include circuitry for measuring amplitudes of resulting currents or voltages, such as sample and hold circuitry.

In these examples, signal generator 84 delivers signals that do not necessarily deliver stimulation therapy to heart 12, due to, for example, the amplitudes of such signals and/or the timing of delivery of such signals. For example, these signals may comprise sub-threshold amplitude signals that may not stimulate heart 12. In some cases, these signals may be delivered during a refractory period, in which case they also may not stimulate heart 12. IMD 16 may use defined or predetermined pulse amplitudes, widths, frequencies, or electrode polarities for the pulses delivered for these various impedance measurements. In some examples, the amplitudes and/or widths of the pulses may be sub-threshold, e.g., below a threshold necessary to capture or otherwise activate tissue, such as cardiac tissue.

In certain cases, IMD 16 may measure impedance values that include both a resistive and a reactive (i.e., phase) component. In such cases, IMD 16 may measure impedance during delivery of a sinusoidal or other time varying signal by signal generator 84, for example. Thus, as used herein, the term "impedance" is used in a broad sense to indicate any collected, measured, and/or calculated value that may include one or both of resistive and reactive components. Impedance data may include actual, measured impedance values, or may include values that can be used to calculate impedance (such as current and/or voltage values).

In some examples in which impedance measurement module 106 measures impedance values including both a resistive and reactive component, processor 80 may process digitized versions of these signals to separate the real and reactive components. In other examples, impedance measurement module 106 may include circuitry to selective provide one or both of the real or reactive components. For example, impedance measurement module 106 may include one or more chopper stabilized instrumentation amplifiers for selectively providing one or both the real or reactive components. An example, chopper stabilized instrumentation amplifier for this purpose is described in commonly-assigned U.S. Pat. No. 7,391,257 to Denison et al., entitled "CHOPPER-STABILIZED INSTRUMENTATION AMPLIFIER FOR IMPEDANCE MEASUREMENT," which issued on Jun. 24, 2008, and is incorporated herein by reference in its entirety.

In some examples, impedance measurement block 106 may isolate a real component of the impedance to assist in the determination of impedance values. Impedance measurement block 106 may gather impedance measurements from multiple combinations of electrodes either simultaneously or at specified time intervals depending on the instructions received by electrical sensing module 86 from processor 80.

Figure 8:
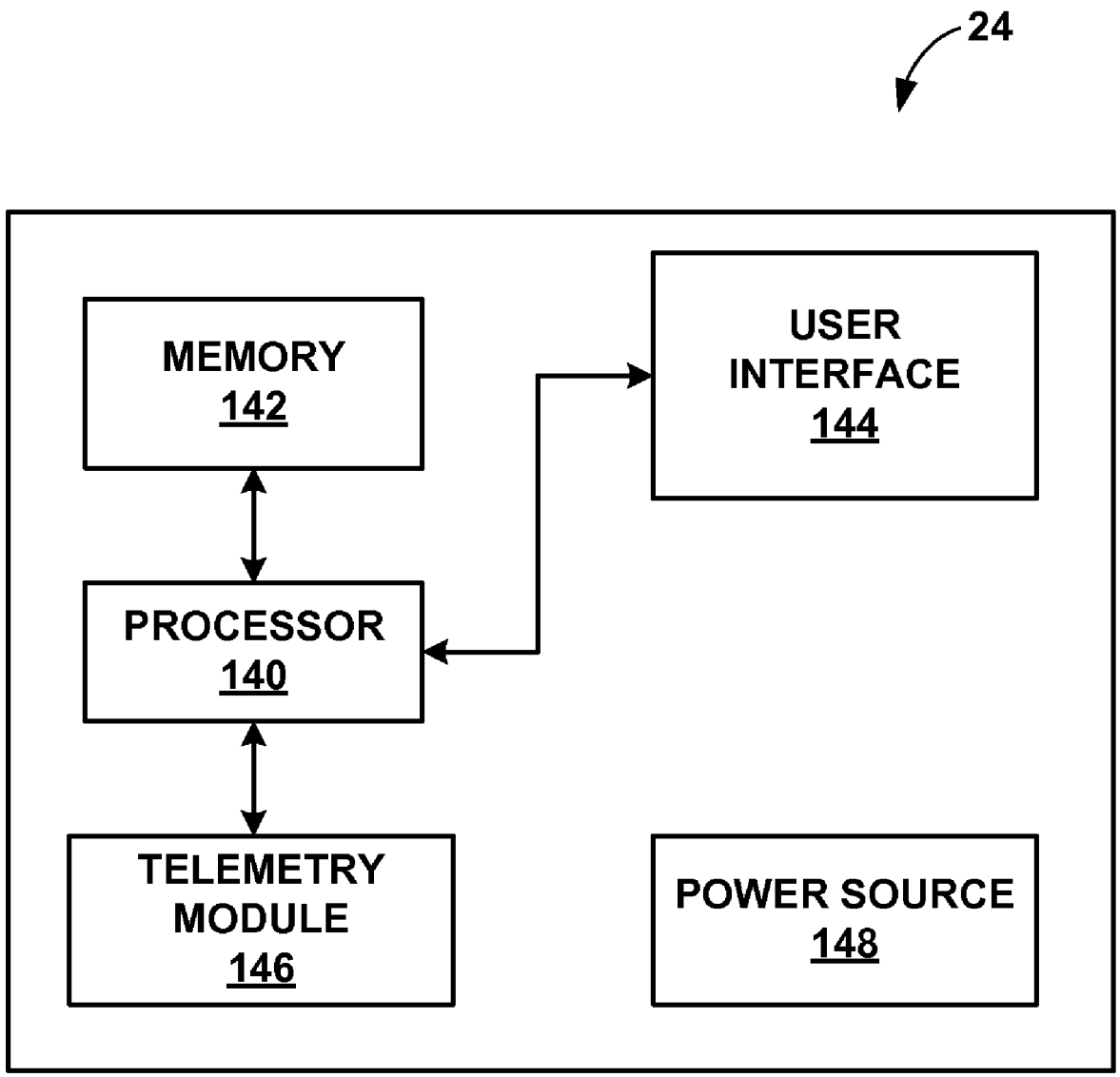
FIG. 8 is block diagram illustrating an example programmer.

FIG. 8 is block diagram illustrating an example programmer 24. In general, a programmer may be a computing device. As shown in FIG. 8, programmer 24 includes processor 140, memory 142, user interface 144, telemetry module 146, and power source 148. Programmer 24 may be a dedicated hardware device with dedicated software for programming of IMD 16. Alternatively, programmer 24 may be an off-the-shelf computing device running an application that enables programmer 24 to program IMD 16.

A user may use programmer 24 to select therapy programs (e.g., sets of stimulation parameters), generate new therapy programs, modify therapy programs through individual or global adjustments or transmit the new programs to a medical device, such as IMD 16 (FIG. 1). The clinician may interact with programmer 24 via user interface 144 which may include display to present graphical user interface to a user, and a keypad or another mechanism for receiving input from a user.

Processor 14 can take the form of one or more microprocessors, DSPs, ASICs, FPGAs, programmable logic circuitry, or the like, and the functions attributed to processor 102 herein may be embodied as hardware, firmware, software or any combination thereof. Memory 142 may store instructions that cause processor 140 to provide the functionality ascribed to programmer 24 herein, and information used by processor 140 to provide the functionality ascribed to programmer 24 herein. Additionally, processor 140 may perform the functionality of either or all of control unit 92, impedance parameter module 94, or comparison module 95 described with respect to FIG. 6.

Memory 142 may include any fixed or removable magnetic, optical, or electrical media, such as RAM, ROM, CD-ROM, hard or floppy magnetic disks, EEPROM, or the like. Memory 142 may also include a removable memory portion that may be used to provide memory updates or increases in memory capacities. A removable memory may also allow patient data to be easily transferred to another computing device, or to be removed before programmer 24 is used to program therapy for another patient. Memory 142 may also store information that controls therapy delivery by IMD 16, such as stimulation parameter values.

Programmer 24 may communicate wirelessly with IMD 16, such as by using RF communication or proximal inductive interaction. This wireless communication is possible through the use of telemetry module 102, which may be coupled to an internal antenna or an external antenna. An external antenna that is coupled to programmer 24 may correspond to the programming head that may be placed over heart 12, as described above with reference to FIG. 1. Telemetry module 142 may be similar to telemetry module 88 of IMD 16 (FIG. 4).

Telemetry module 142 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a server capable of processing information retrieved from IMD 16. An example of such an example is discussed with respect to FIG. 9.

Processor 140 of programmer 24 may implement any of the techniques described herein, or otherwise perform any of the methods described below. For example, processor 140 of programmer 24 may determine impedance parameter values, compare the impedance parameter values, or identify a change in hemodynamic status using any of the techniques described herein, based on impedance measurements received from IMD 16. Processor 140 of programmer 24 may, in some examples, control the timing and configuration of impedance measurements by IMD 16.

Figure 9:
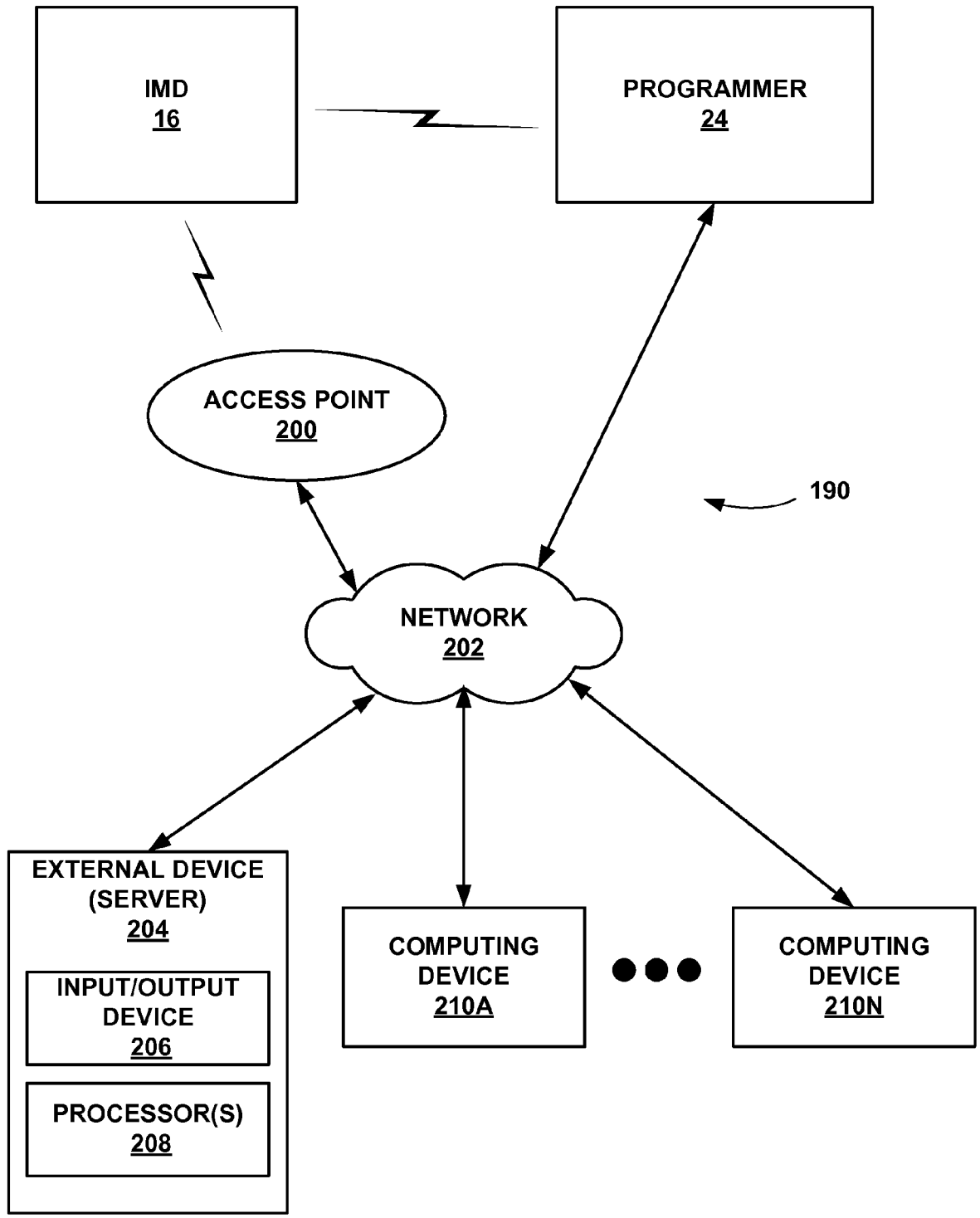
FIG. 9 is a block diagram illustrating an example system that includes an external device, such as a server, and one or more computing devices that are coupled to the IMD and the programmer shown in FIG. 1 via a network.

FIG. 9 is a block diagram illustrating an example system 190 that includes an external device, such as a server 204, and one or more computing devices 210A-210N (computing devices 210), that are coupled to the IMD 16 and programmer 24 shown in FIG. 1 via a network 202. In this example, IMD 16 may use its telemetry module 88 to communicate with programmer 24 via a first wireless connection, and to communication with an access point 200 via a second wireless connection. In the example of FIG. 9, access point 200, programmer 24, server 204, and computing devices 210 are interconnected, and able to communicate with each other, through network 202. In some cases, one or more of access point 200, programmer 24, server 204, and computing devices 210 may be coupled to network 202 through one or more wireless connections. IMD 16, programmer 24, server 204, and computing devices 210 may each comprise one or more processors, such as one or more microprocessors, DSPs, ASICs, FPGAs, programmable logic circuitry, or the like, that may perform various functions and operations, such as those described herein.

Access point 200 may comprise a device that connects to network 186 via any of a variety of connections, such as telephone dial-up, digital subscriber line (DSL), or cable modem connections. In other examples, access point 200 may be coupled to network 202 through different forms of connections, including wired or wireless connections. In some examples, access point 200 may be co-located with patient 14 and may comprise one or more programming units and/or computing devices (e.g., one or more monitoring units) that may perform various functions and operations described herein. For example, access point 200 may include a home-monitoring unit that is co-located with patient 14 and that may monitor the activity of IMD 16.

In some examples, access point 200, server 204 or computing devices 210 may perform any of the various functions or operations described herein. For example, processor 208 of server 204 may estimate pressures or volumes using any of the techniques herein based on impedance measurements received from IMD 16 via network 202. Processor 208 of server 204 may, in some examples, control the timing and configuration of impedance measurements by IMD 16 via network 202 and access point 200.

In some cases, server 204 may be configured to provide a secure storage site for historical data 97 (FIG. 4) that has been collected from IMD 16 and/or programmer 24. Network 202 may comprise a local area network, wide area network, or global network, such as the Internet. In some cases, programmer 24 or server 206 may assemble historical data 97 in web pages or other documents for viewing by and trained professionals, such as clinicians, or by the patient, via viewing terminals associated with computing devices 210. The illustrated system of FIG. 9 may be implemented, in some aspects, with general network technology and functionality similar to that provided by the Medtronic CareLink® Network developed by Medtronic, Inc., of Minneapolis, Minn.

Figure 10:
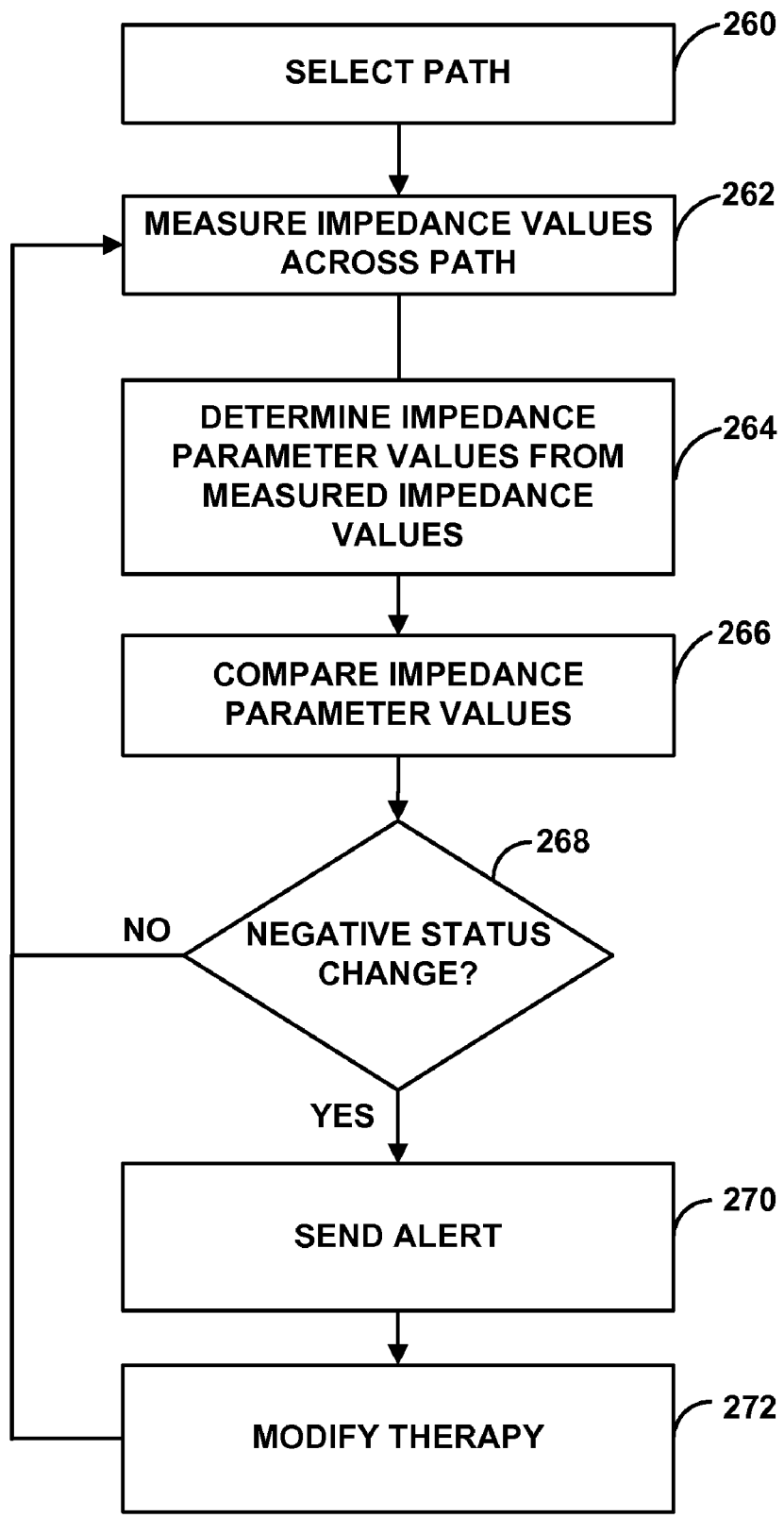
FIG. 10 is a flow diagram illustrating an example technique for identifying a change in a cardiovascular parameter based on a comparison of impedance parameter values.

FIG. 10 is a flow diagram illustrating an example technique for identifying a change in a cardiovascular parameter based on a comparison of impedance parameter values. The techniques of FIGS. 10-13 and 15 are discussed with respect to IMD 16 of FIG. 1, however it should be understood that similar techniques may be performed by a similar IMD, or the IMD or medical device or other components of therapy systems 218 of FIGS. 4A-4C or therapy system 240 of FIG. 5.

Initially, IMD 16 is implanted in patient 14 such that electrodes, e.g. electrodes 62, 64, and/or 66, may form an electrical path through a cardiac chamber or a blood vessel, such as the aorta. IMD 16 may select this electrical path for an impedance measurement. (260). IMD 16 may be configured to periodically create a voltage across two of the electrodes, a current between the electrodes, or some other method to establish a path between two of the electrodes. In any case, IMD 16 may select a path between two of the electrodes that can be used to determine an impedance value across the path. Additional electrodes may be used as discussed herein to reduce or eliminate noise from other tissue and bodily structure near the cardiac chamber or blood vessel of interest.

After a path has been selected, IMD 16 may begin measuring impedance values through the path (262). IMD 16 may, for example, create a voltage between two electrodes and calculate the resulting current through the path to measure the impedance. As another example, IMD 16 may deliver a known current through the path and calculate the voltage between the electrodes to measure the impedance. IMD 16 may also use other methods as discussed herein to measure the impedance of the path through the cardiac chamber or blood vessel.

IMD 16 may determine impedance parameter values based on the impedance values (264). IMD 16 may, for example, determine a cardiac cycle corresponding to the measured impedance values. IMD 16 may further determine whether the most recently measured impedance value is part of the same cardiac cycle as an earlier measured impedance value, or whether the most recently measured impedance value is part of a new cardiac cycle. Impedance parameter values may include, for example, a mean of the impedance values for a cardiac cycle, an amplitude of the impedance values for a cardiac cycle, a range between the maximum impedance value and the minimum impedance value for a cardiac cycle, a maximum of a first derivative of the impedances for a cardiac cycle, or other values. Example impedance parameter values are discussed with respect to FIGS. 11-13 and 15.

IMD 16 may compare two or more impedance parameter values (266). For example, IMD 16 may determine a difference between an impedance parameter value for a current cardiac cycle and an impedance parameter value for a previous cardiac cycle, or a difference between an impedance parameter value for a current cardiac cycle and a mean or median of impedance parameter values for a plurality of previous cardiac cycles. Various features of the comparison, i.e. the difference, may be used to identify a change in a cardiovascular parameter. In particular, IMD 16 may determine whether the difference indicates a potential problem for the patient (268). For example, for certain impedance parameter values, a change in the positive direction may indicate an onset or worsening of a condition, for other impedance parameter values, a change in the negative direction may indicate an onset or worsening of a condition, and for other impedance parameter values, a difference in either direction may indicate an onset or worsening of a condition. One or more thresholds may be used to determine whether the difference is significant enough to indicate onset or worsening of a condition.

Although the comparison is described herein with reference to a difference between a current impedance parameter value and one or more previous impedance parameter values, in other examples the comparison may include determining a ratio or percentage of a current value to a previous value, or a mean or median of a plurality of previous values. The ratio or percentage may be compared to one or more thresholds to determine whether the difference is significant enough to indicate onset or worsening of a condition.

When the comparison does not indicate a problem ("NO" branch of 268), IMD 16 may continue measuring impedance values and determining impedance parameter values for comparison. However, when the comparison indicates a problem, ("YES" branch of 268), IMD 16 may send an alert, e.g. to programmer 24 (270). Additionally, or in the alternative, IMD 16 may modify a therapy in response to the change in the cardiovascular parameter. IMD 16 may then continue measure the impedance across the path (262) during subsequent cardiac cycles.

Figure 11:
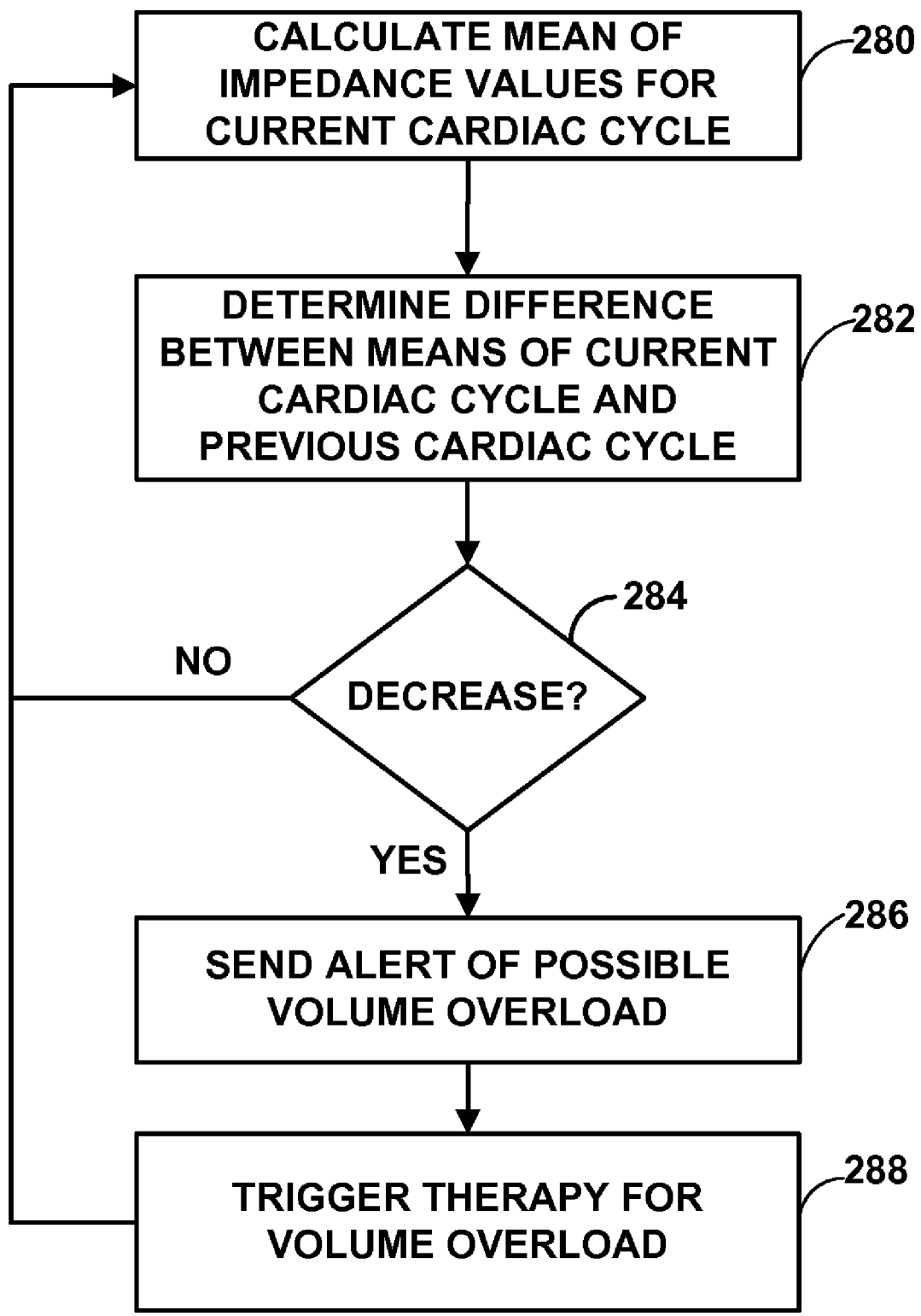
FIG. 11 is a flow diagram illustrating an example technique for using a mean of impedance values over a cardiac cycle to identify a change in a cardiovascular parameter.

FIG. 11 is a flow diagram illustrating an example technique for using a mean of impedance values over a cardiac cycle to identify a change in a cardiovascular parameter. IMD 16 may determine a mean of the measured impedance values as an impedance parameter for the current cardiac cycle (280). IMD 16 may then compare the mean of the current cardiac cycle to a mean of a previous cardiac cycle, such as the last cardiac cycle (282). If the mean of the impedance values for the current cardiac cycle remained the same (i.e. did not decrease) ("NO" branch of 284) relative to the previous cardiac cycle, IMD 16 may determine a mean of the impedance values for the next cardiac cycle. However, if the mean of the impedance values for the current cardiac cycle decreased ("YES" branch of 284), IMD 16 may send an alert of a possible volume overload (286). Additionally, or in the alternative, IMD 16 may modify a treatment by triggering or changing a therapy to treat volume overload (288). IMD 16 may continue calculating mean impedances (280) for subsequent cardiac cycles and performing the method of FIG. 11.

Figure 12:
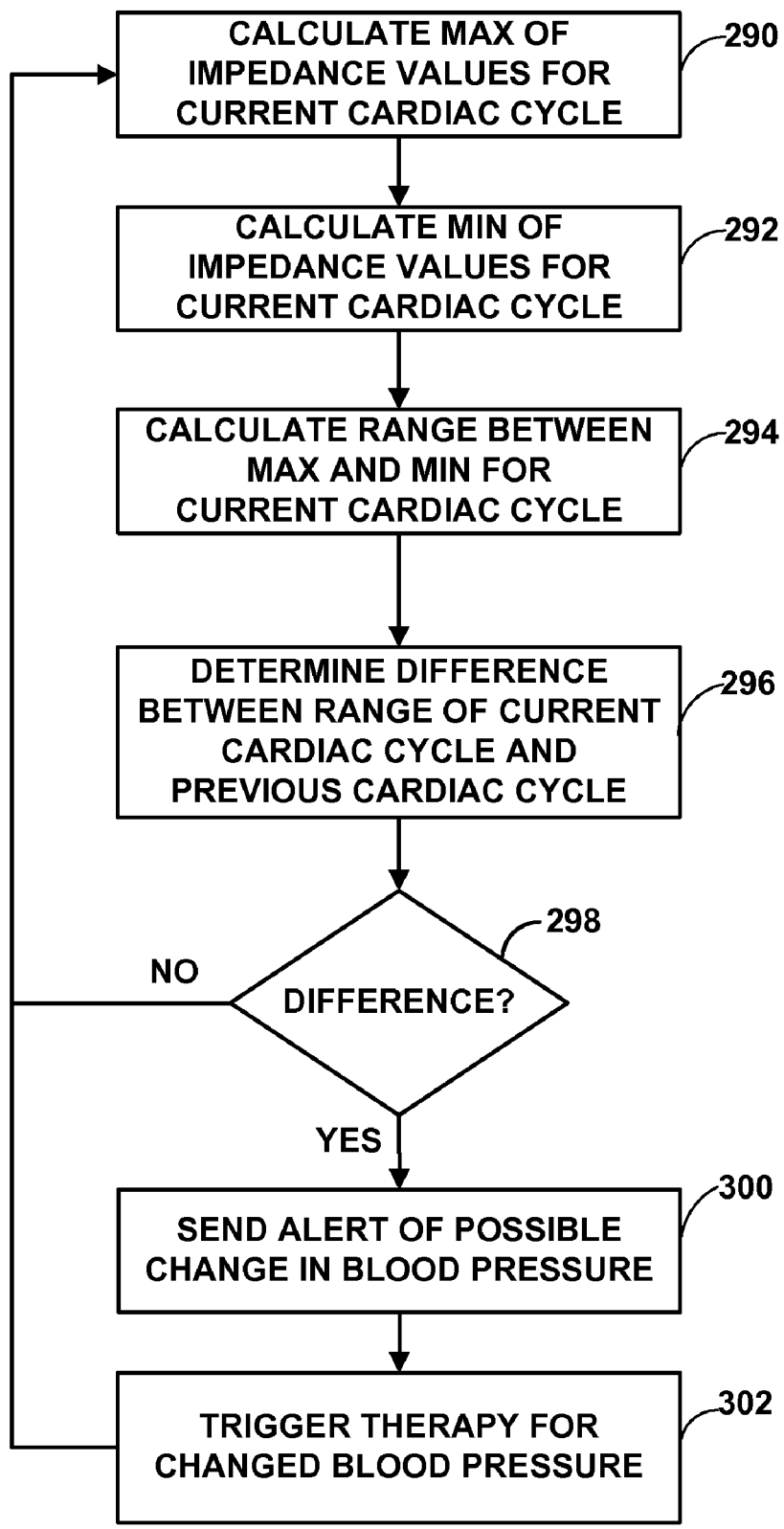
FIG. 12 is a flow diagram illustrating an example technique for using a range between local maxima and minima of a cardiac cycle to identify a change in a cardiovascular parameter.

FIG. 12 is a flowchart illustrating an example technique for using a range between local maxima and minima of a cardiac cycle to identify a change in a cardiovascular parameter. Initially, IMD 16 may determine a maximum impedance value for the current cardiac cycle (290). IMD 16 may then determine a minimum impedance value for the current cardiac cycle (292). IMD 16 may calculate the difference between the maximum and the minimum to determine a range for the current cardiac cycle (294). IMD 16 may then determine the difference between the range for the current cardiac cycle and the range for a previous cardiac cycle (296). In one example, IMD 16 may determine that the difference is significant if the difference exceeds a threshold, such as a certain percentage difference. A difference in the ranges may indicate a change in the patient's blood pressure. Accordingly, if there is a difference ("YES" branch of 298), IMD 16 may send an alert of a possible change in the patient's blood pressure (300). IMD 16 may additionally, or in the alternative, trigger a treatment for the difference in blood pressure (302). In one example, for example, IMD 16 may trigger a treatment for increased blood pressure when the difference indicates an increase in blood pressure. IMD 16 may continue calculating the impedance range for subsequent cardiac cycles (290-294) and performing the method of FIG. 12.

Figure 13:
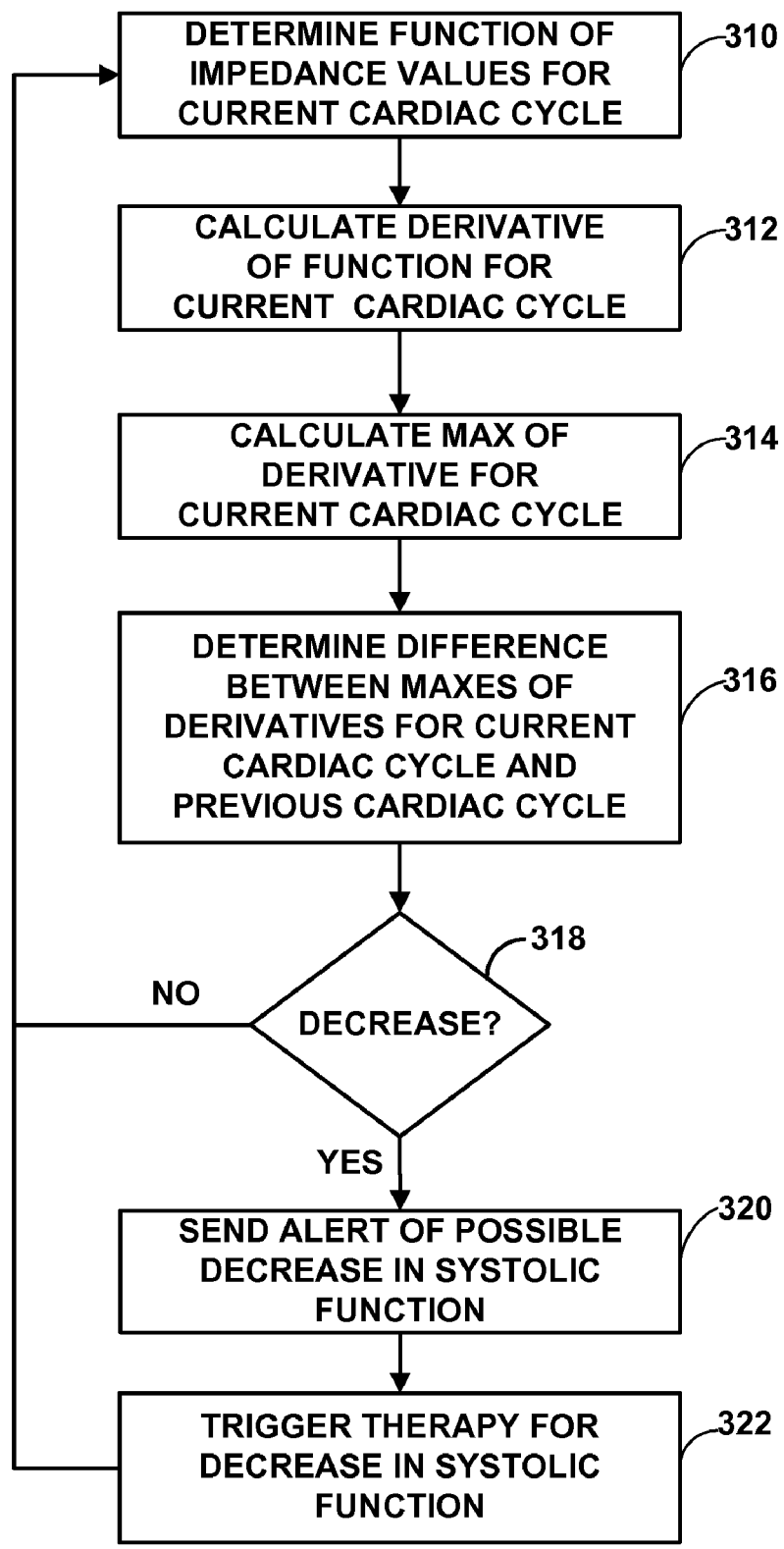
FIG. 13 is a flow diagram illustrating an example technique for using a maximum of a first derivative of a function of the measured impedance values of a cardiac cycle to identify a change in a cardiovascular parameter.

FIG. 13 is a flowchart illustrating an example technique for using a maximum of a first derivative of a function of the measured impedance values of a cardiac cycle to identify a change in a cardiovascular parameter. Initially, IMD 16 may determine a function corresponding to the measured impedance values (310). IMD 16 may determine a function that best fits the measured impedance values for the current cardiac cycle. In one example, the function may be a waveform function. In another example, the function may be a portion of a polynomial with a degree of three. In another example, the function may be a function that best fits the measured impedance values.

In any case, after IMD 16 has determined the function corresponding to the measured impedance values, IMD 16 may calculate the derivative of the function (312). IMD 16 may then determine the maximum value of the derivative (314). IMD 16 may then compare the maximum of the derivative of the function for the current cardiac cycle to the maximum of the derivative of a function for a previous cardiac cycle (316). If there is no change in the maximum for the current cardiac cycle ("NO" branch of 318), IMD 16 may calculate the function and the derivative, and the corresponding maximum, for the next cardiac cycle. However, a decrease in the maximum for the current cardiac cycle may indicate a decrease in systolic function. Therefore, when IMD 16 detects a decrease in the maximum for the current cardiac cycle ("YES" branch of 318), IMD 16 may send an alert of a possible decrease in systolic function (320). Additionally, or in the alternative, IMD 16 may modify a therapy to treat a decrease in systolic function (322). IMD 16 may continue calculating the impedance derivative (310, 312) for subsequent cardiac cycles and performing the method of FIG. 13.

Figure 14:
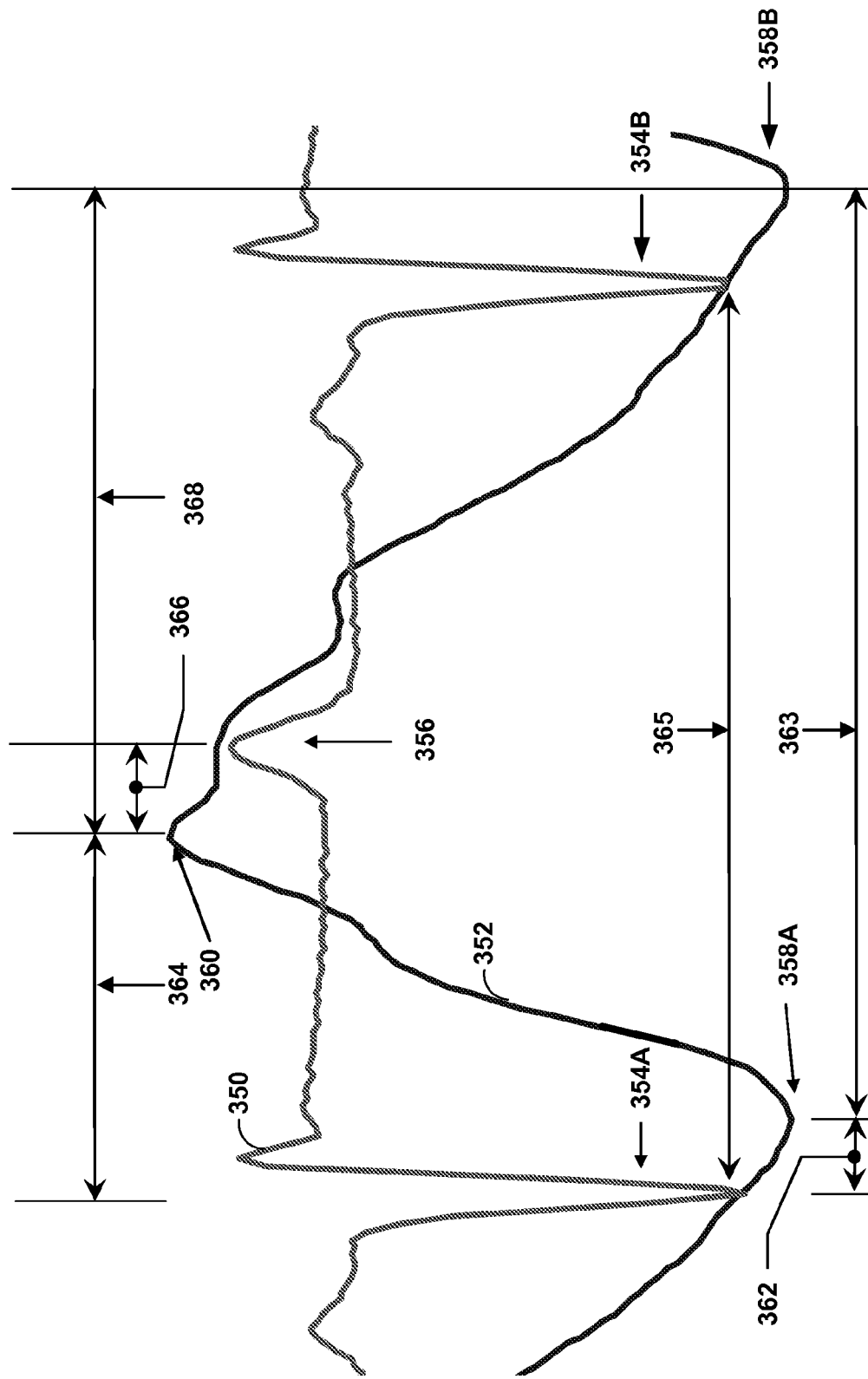
FIG. 14 is a graph illustrating a cardiac electrogram and an impedance waveform that depicts a time interval between a cardiac event and fiducial points of the impedance waveform.

FIG. 14 is a graph illustrating a cardiac electrogram (EGM) 350 and a conductance waveform 352 for a cardiac cycle. A conductance waveform is a reciprocal of an impedance waveform. That is, to determine a conductance waveform w(x) from impedance waveform z(x), w(x)=1/z(x). Thus, as used herein, the term "impedance values" may be understood to include conductance values, i.e. values that are the reciprocal of an impedance value.

The graph of FIG. 14 also depicts time intervals between fiducial points of EGM 350 and fiducial points of conductance waveform 352 for the cardiac cycle. In particular, example EGM 350 of FIG. 14 includes fiducial points corresponding to cardiac electrical events, such as R-wave 354A and T-wave 356. Conductance waveform 352 includes fiducial points such as conductance minimum 358A and conductance maximum 360 for the cardiac cycle.

In one example, IMD 16 may detect EGM 350 and conductance waveform 352 using any of the techniques described herein. IMD 16 may identify fiducial points, such as R-wave 354A, conductance minimum 358A and conductance maximum 360. As one example, IMD 16 may identify R-waves 354A and 354B (collectively "R-waves 354") and T-wave 356 based on indications received from one or more of narrow band channels 102 (FIG. 7), or based on digital signal processing of a signal received by wide band channel 104 (FIG. 7).

R-wave 354A and R-wave 354B may be fiducial points of distinct cardiac cycles. That is, R-wave 354A and R-wave 354B may occur in two distinct cardiac cycles. In any case, IMD 16 may identify R-wave 354A for a cardiac cycle. IMD 16 may also identify minimum 358A of conductance waveform 352 and maximum 360 of conductance waveform 352. In one example, IMD 16 identifies local minima and local maxima for the current cardiac cycle, e.g. between R-wave 354A and R-wave 354B, using any known technique for identifying minima and maxima in a signal.

IMD 16 may further determine time interval 362 between R-wave 354A and minimum 358A and/or time interval 364 between R-wave 354A and conductance maximum 360. IMD 16 may also determine time interval 366 between conductance maximum 360 and EGM maximum 356. IMD 16 may also determine interval 368 between conductance maximum 360 and conductance minimum 358B. IMD 16 may also determine interval 365 between R-Wave 354A and R-Wave 354B. IMD 16 may also determine interval 363 between conductance minimum 358A and conductance minimum 358B.

In one example, IMD 16 may determine only time interval 362. In one example, IMD 16 may only determine time interval 364. In one example, IMD 16 may determine both time interval 362 and time interval 364. In one example, IMD 16 may determine both time interval 362 and time interval 364, and IMD 16 may further determine a ratio between time interval 362 and time interval 364. Experimental data have shown that variations in time intervals, such as time interval 362 and time interval 364, may indicate an increase in afterload or vascular tone, which indicates a possibility of hypertension. IMD 16 may define various ratios between any of intervals 362, 364, 430, 432, 434, and 436. The ratio between interval 362 and interval 364, as one example, may be referred to as the vascular tone index (VTI).

Figure 15:
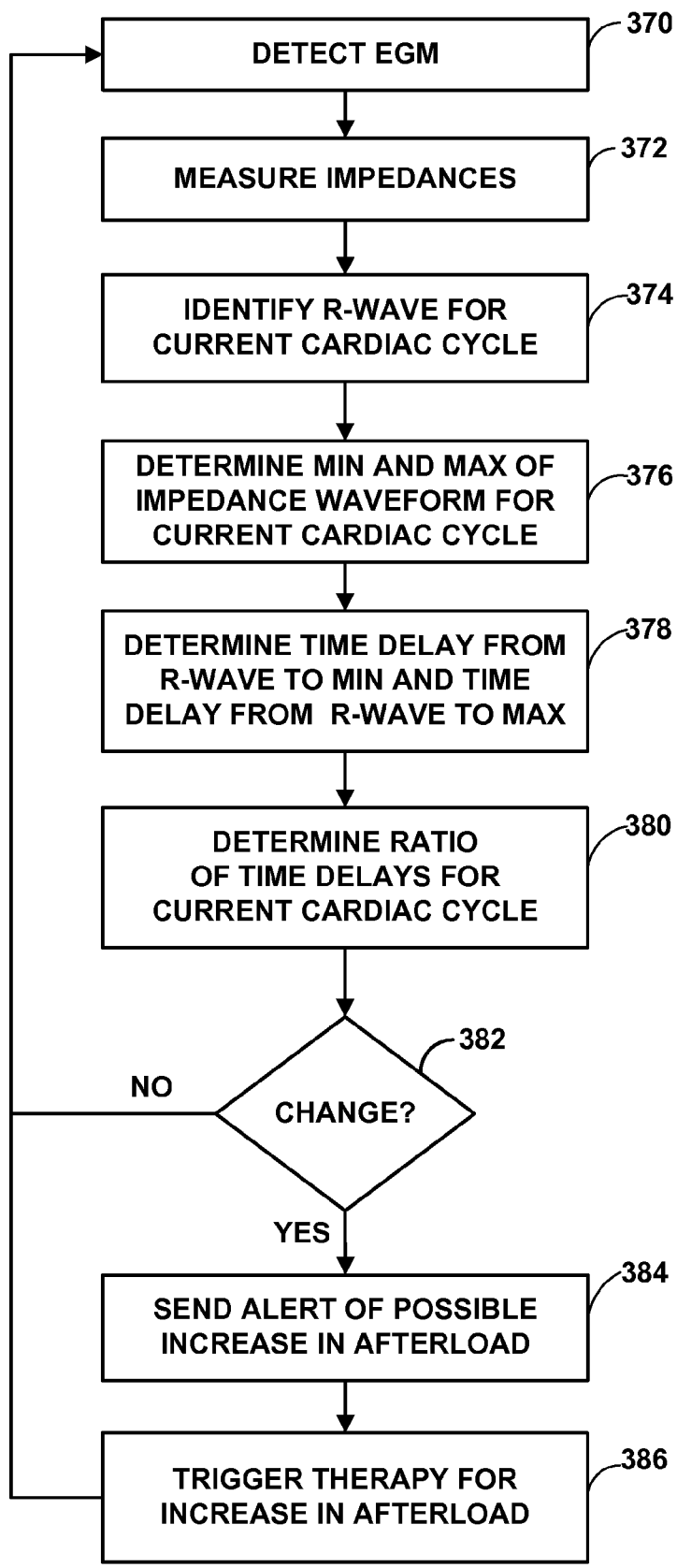
FIG. 15 is a flow diagram illustrating an example technique for using cardiac event and an impedance waveform to identify a change in a cardiovascular parameter.

FIG. 15 is a flow diagram illustrating an example technique for using cardiac electrical signals and measured path impedance values to identify a change in a cardiovascular parameter. Initially, IMD 16 may detect cardiac electrical signals (370) and measure impedances (372), e.g. by via any combination of electrodes 40, 42, 44, 46, 48, 50, 58, 62, 64, and 66, as described above. For each cardiac cycle, IMD 16 may identify fiducial points of the cardiac electrical signal, and of a portion of an impedance waveform comprising the measured impedance values, corresponding to a cardiac cycle. In the example of FIG. 15, IMD 16 identifies an R-wave for the cardiac cycle (374). IMD 16 may also identify a minimum impedance value for the cardiac cycle and a maximum impedance value for the current cardiac cycle (376).

IMD 16 may then determine time intervals from the R-wave to the minimum impedance value and from the R-wave to the maximum impedance value for the current cardiac cycle (378). IMD 16 may also calculate a ratio of the time interval from the R-wave to the minimum impedance and the time interval from the R-wave to the maximum impedance, e.g. calculate the VTI (380). In other examples, IMD 16 may identify other impedance parameters, such as just the time interval for either the R-wave to the minimum, the R-wave to the maximum, both the time interval for the R-wave to the minimum and the time interval for the R-wave to the maximum, a difference between the time intervals, or other impedance parameters.

In the example, IMD 16 may store a value for the ratio as an impedance parameter for each cardiac cycle, e.g. in historical data 97 of memory 82. IMD 16 may then compare the ratio for the current cardiac cycle to the ratio for one or more earlier cardiac cycles (382). In one example, IMD 16 may compare the ratio for the current cardiac cycle to an average ratio for earlier cardiac cycles. In any case, where the ratio has changed, e.g. a change in the ratio for the current cardiac cycle exceeds a threshold difference from the ratio used for comparison ("YES" branch of 382), IMD 16 may determine that there is a possibility of an increase in afterload of patient 14. Therefore, IMD 16 may send an alert of a possible change in afterload (384) and/or trigger a therapy for an increase in afterload (386). After treatment, or where there has not been a change in the ratio for the current cardiac cycle ("NO" branch of 382), IMD 16 may continue to monitor data for the next cardiac cycle.

Although described in the context of measuring an interval between an R-wave and fiduciary points in an impedance waveform, in other examples the technique of FIG. 15 may be applied to measurements of one or more intervals between any mechanical or electrical cardiac event, which may be detected in any manner, and one or more fiduciary points in an impedance or conductance waveform. For example, IMD 16 may identify other fiducial points, such as only a local minimum (i.e. a minimum of the impedance values for the current cardiac cycle), only a local maximum, or a P-wave or T-wave for a cardiac cycle. In still other examples, IMD 16 may identify fiducial points of a first derivative of the impedance waveform, such as a maximum or a minimum of the first derivative of the impedance waveform. In other examples, IMD 16 may identify fiducial points of a conductance waveform, determined from the inverse of an impedance waveform, i.e. conductance(x)=1/impedance(x), or the derivative of the conductance waveform. In various examples, IMD 16 and/or another device may employ the example method of FIG. 15, or a similar method, to determine intervals between any cardiac event(s) and/or fiducial points described herein, and in some examples to further determine one or more ratios between such intervals.

Figure 16:
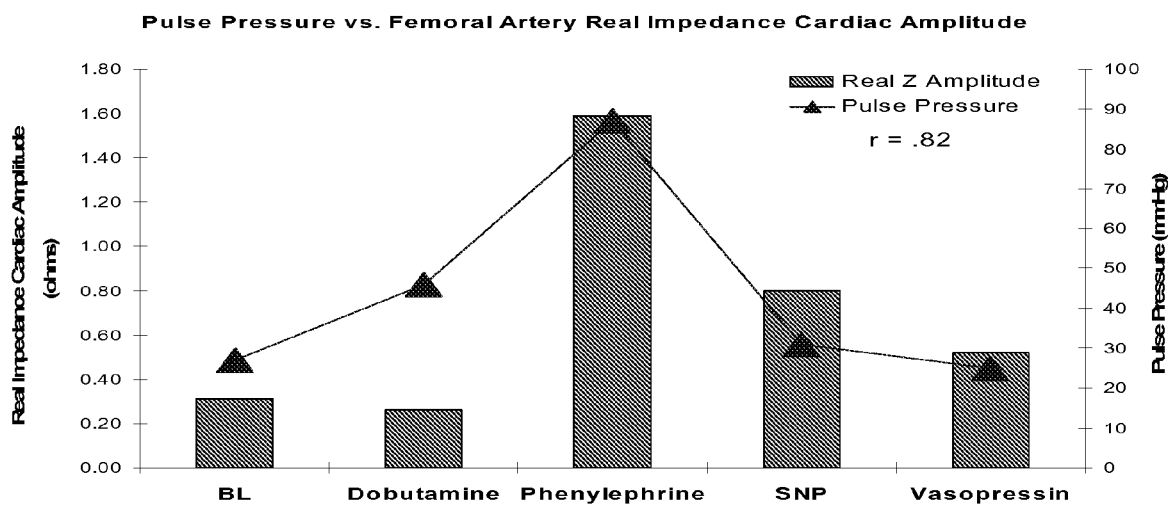
FIG. 16 is a graph illustrating experimental data relating to experimental drug interventions administered compared to baseline for both aortic pulse pressure and impedance amplitude measured with electrodes placed subcutaneously over the femoral artery.

FIG. 16 is a graph illustrating experimental data relating to experimental drug interventions administered compared to baseline for both aortic pulse pressure and impedance amplitude (max−min) measured with electrodes placed subcutaneously over the femoral artery. FIG. 16 indicates that there is a strong correlation (r=0.82) in both parameters over the sequential administration of vasocontrictive, vasodilative and inotropic drug interventions. This data suggests that using subcutaneous impedance monitoring methods over the femoral artery may be useful in monitoring a relative change in afterload or systolic function with hypertensive or heart failure patients respectively. As shown in the graph, all drugs that produced a change in vascular resistance (phenylephrine, sodium nitroprusside and vasopressin), produced a correlated change in pulse pressure and impedance amplitude. More specifically, compared to the previous intervention, if pulse pressure decrease, the impedance amplitude also decreased.

Figure 17:
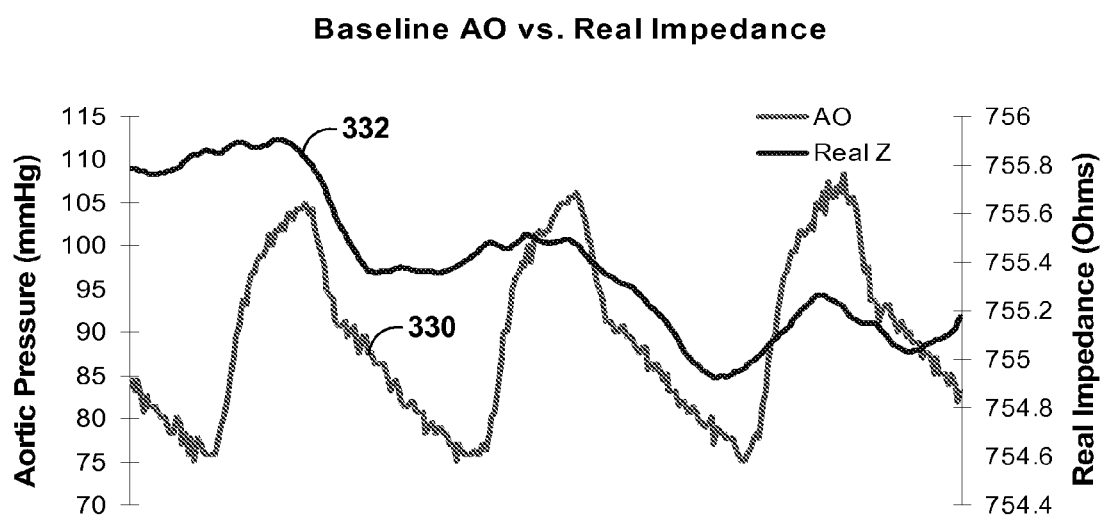
FIG. 17 is a graph illustrating experimental data relating to aortic pressure and impedance waveform morphologies measured in one anesthetized porcine over three cardiac cycles during expiration with a subcutaneous electrode array positioned over the femoral artery.

FIG. 17 is a graph illustrating experimental data relating to aortic pressure and impedance waveform morphologies measured in one anesthetized porcine over three cardiac cycles during expiration with a subcutaneous electrode array positioned over the femoral artery. Baseline aortic pressure (measured in the ascending aorta) waveform 330 and the corresponding real component of complex impedance waveform 332, measured with a bipolar subcutaneous electrode array and complex impedance circuit (4 kHz stimulation frequency@8.5 μA). During baseline, pulse pressure=27 mmHg and impedance magnitude=0.31 ohms. As shown in FIG. 17, for each aortic pulse there is a corresponding impedance pulse.

Figure 18:
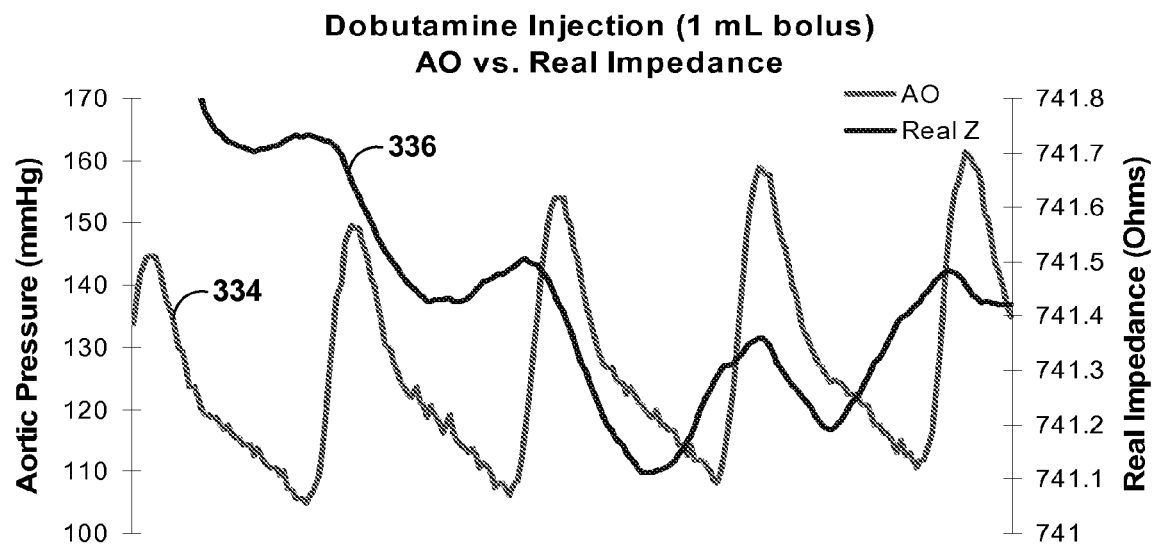
FIG. 18 is a graph illustrating experimental data relating to aortic pressure and impedance waveform morphologies measured in the same anesthetized porcine as in FIG. 15 over four cardiac cycles during expiration with a subcutaneous electrode array positioned over the femoral artery.

FIG. 18 is a graph illustrating experimental data relating to aortic pressure and impedance waveform morphologies measured in the same anesthetized porcine as in FIG. 15 over four cardiac cycles during expiration with a subcutaneous electrode array positioned over the femoral artery. Dobutamine (positive inotrope) was administered via a 1 mL bolus IV. This drug intervention generates a change (compared to baseline) in aortic pressure amplitude 334 and the corresponding real component of complex impedance 336 measured 30 seconds after IV infusion. During the dobutamine bolus injection, pulse pressure increased from baseline (27 mmHg) to 46 mmHg suggesting an increase in stroke volume due to the drug intervention while impedance magnitude decreased slightly to 0.26 ohms. This slight decrease in impedance magnitude may be due to the mild decrease in systemic vascular resistance often associated with the administration of dobutamine. However, mean impedance decreased suggesting an increase in vascular volume due to increased contractility and subsequent stroke volume. As shown in FIG. 18, for each aortic pulse there is a corresponding impedance pulse. Furthermore, the slope of the impedance waveform increased compared to the baseline impedance waveform as suspected from administration of the positive inotrope.

Figure 19:
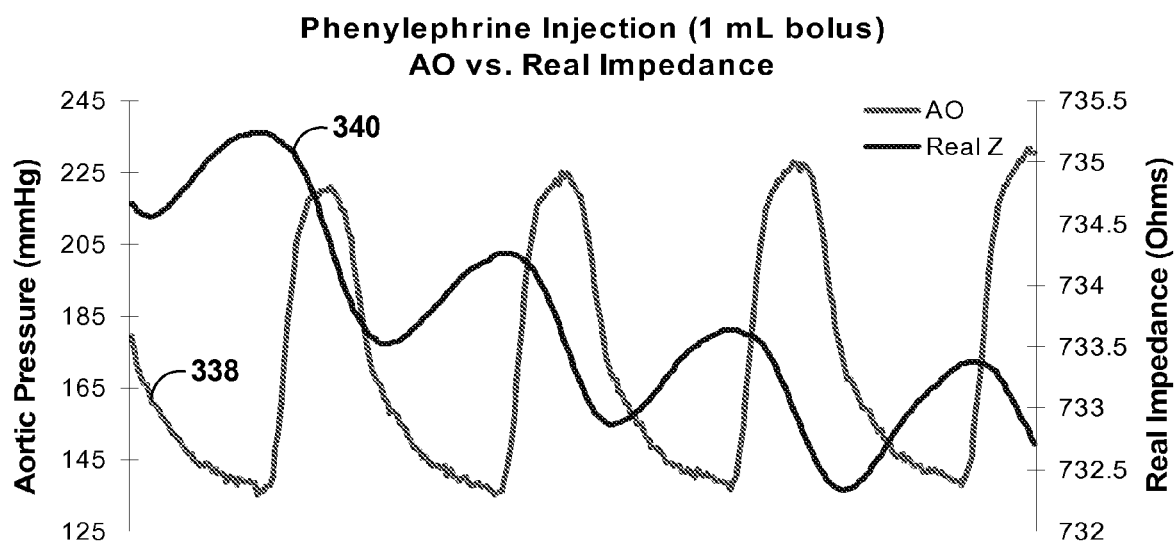
FIG. 19 is another graph illustrating other experimental data relating to aortic pressure and impedance waveform morphologies measured in the same anesthetized porcine as in FIG. 17 over four cardiac cycles during expiration with a subcutaneous electrode array positioned over the femoral artery.

FIG. 19 is a graph illustrating experimental data relating to aortic pressure and impedance waveform morphologies measured in the same anesthetized porcine as in FIG. 17 over four cardiac cycles during expiration with a subcutaneous electrode array positioned over the femoral artery. Phenylephrine (vasoconstrictor) was administered via a 1 mL bolus IV. This drug intervention generates a change (compared to baseline and dobutamine) in aortic pressure amplitude 338 and the corresponding real component of complex impedance 340 measured 30 seconds after IV infusion. During the phenylephrine bolus injection, pulse pressure increased to 87 mmHg due to the vasoconstrictive properties of the drug and impedance magnitude generated a corresponding increase to 1.59 ohms. As shown in FIG. 19, for each aortic pulse there is a corresponding impedance pulse.

Figure 20:
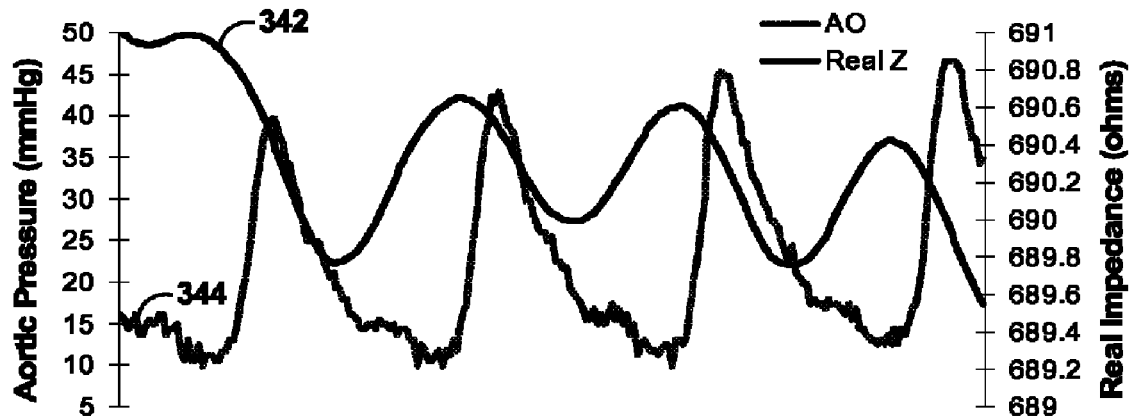
FIG. 20 is another graph illustrating other experimental data relating to aortic pressure and impedance waveform morphologies measured in the same anesthetized porcine as in FIG. 17 over four cardiac cycles during expiration with a subcutaneous electrode array positioned over the femoral artery.

FIG. 20 is a graph illustrating experimental data relating to aortic pressure and impedance waveform morphologies measured in the same anesthetized porcine as in FIG. 17 over four cardiac cycles during expiration with a subcutaneous electrode array positioned over the femoral artery. Sodium Nitroprusside (vasodilator) was administered via a 1 mL bolus IV. This drug intervention generates a change (compared to the previous intervention) in aortic pressure amplitude 344 and the corresponding real component of complex impedance 342 measured 30 seconds after IV infusion. During the sodium nitroprusside bolus injection, pulse pressure decreased to 31 mmHg due to the vasodialative properties of the drug and impedance magnitude generated a corresponding decrease to 0.80 ohms compared to the phenylephrine intervnetion. As shown in FIG. 20, for each aortic pulse, there is a corresponding impedance pulse.

Figure 21:
FIG. 21 is another graph illustrating other experimental data relating to aortic pressure and impedance waveform morphologies measured in the same anesthetized porcine as in FIG. 17 over four cardiac cycles during expiration with a subcutaneous electrode array positioned over the femoral artery.

FIG. 21 is a graph illustrating experimental data relating to aortic pressure and impedance waveform morphologies measured in the same anesthetized porcine as in FIG. 17 over four cardiac cycles during expiration with a subcutaneous electrode array positioned over the femoral artery. Vasopressin (vasoconstrictor) was administered via a 1 mL bolus IV. This drug intervention generates a change (compared to the previous intervention) in aortic pressure amplitude 348 and the corresponding real component of complex impedance 346 measured 30 seconds after IV infusion. During the vasopressin bolus injection, pulse pressure decreased to 25 mmHg and impedance magnitude generated a corresponding decrease to 0.52 ohms. As shown in FIG. 21, for each aortic pulse there is a corresponding impedance pulse.

Figure 22:
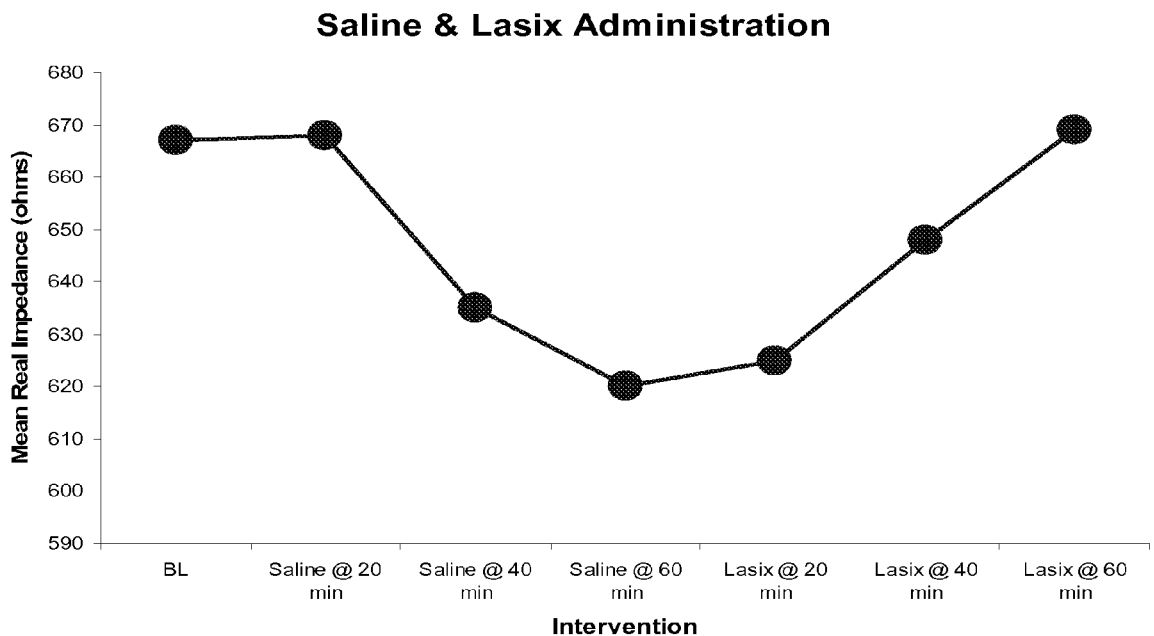
FIG. 22 is a graph illustrating experimental data relating to a change in mean impedance using a bipolar subcutaneous electrode array placed in the thorax intercostal space in one animal.

FIG. 22 is a graph illustrating experimental data relating to a change in mean impedance using a bipolar subcutaneous electrode array placed in the thorax intercostal space in one animal. During this experiment, 1 L of normal saline solution was administered IV over 20 minutes and monitored for an additional 40 minutes. Immediately following, a bolus of Lasix (2-4 mg/kg) was administered IV and monitored for 1 hour. A change in mean resistance of approximately 50 ohms was observed over the one hour saline IV monitoring period and after the bolus Lasix IV injection, returned to baseline values after one additional hour. This data suggest that subcutaneous monitoring of subcutaneous vasculature such as the intercostal vessels, may be useful in monitoring patients with peripheral edema.

Figure 23:
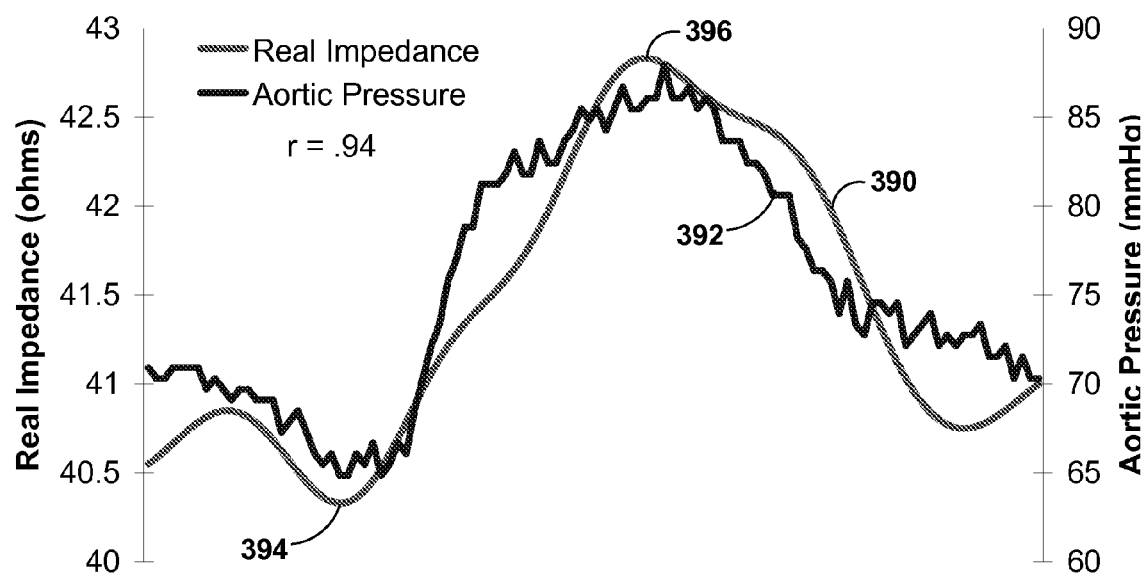
FIG. 23 is a graph illustrating experimental data relating to a change in real time impedance related to aortic pressure.
Figure 24:
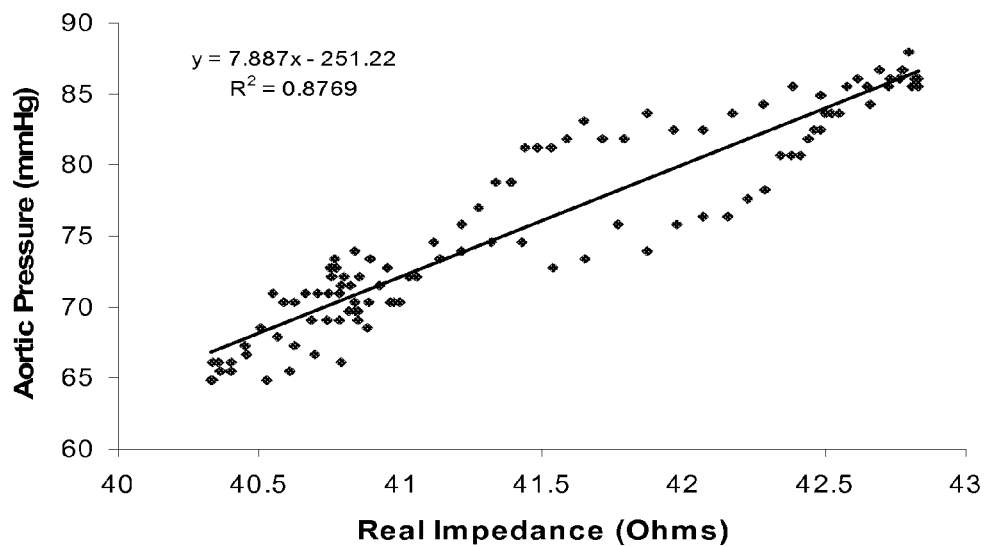
FIG. 24 is a linear regression plot of the data shown in FIG. 23.

FIG. 23 is a graph illustrating experimental data relating to a change in mean impedance related to aortic pressure. The graph of FIG. 23 depicts aortic pressure 392 and impedance 390 waveform morphologies measured in an anesthetized porcine over one cardiac cycle during expiration. A bipolar electrode array (RVcoil-to-Can Emulator) and complex impedance circuit (4 kHz stimulation frequency@8.5 µA) was used to measure cardiac impedance. A Millar catheter, positioned in the ascending aorta was used to measure aortic pressure. Aortic pressure waveform 392 and the corresponding real component of complex impedance waveform 390 have a strong correlation (r=0.94). Impedance minimum 394 correlates to a diastole, while impedance maximum 396 correlates to a systole. FIG. 24 is a linear regression plot of the data shown in FIG. 23.

Figure 25:
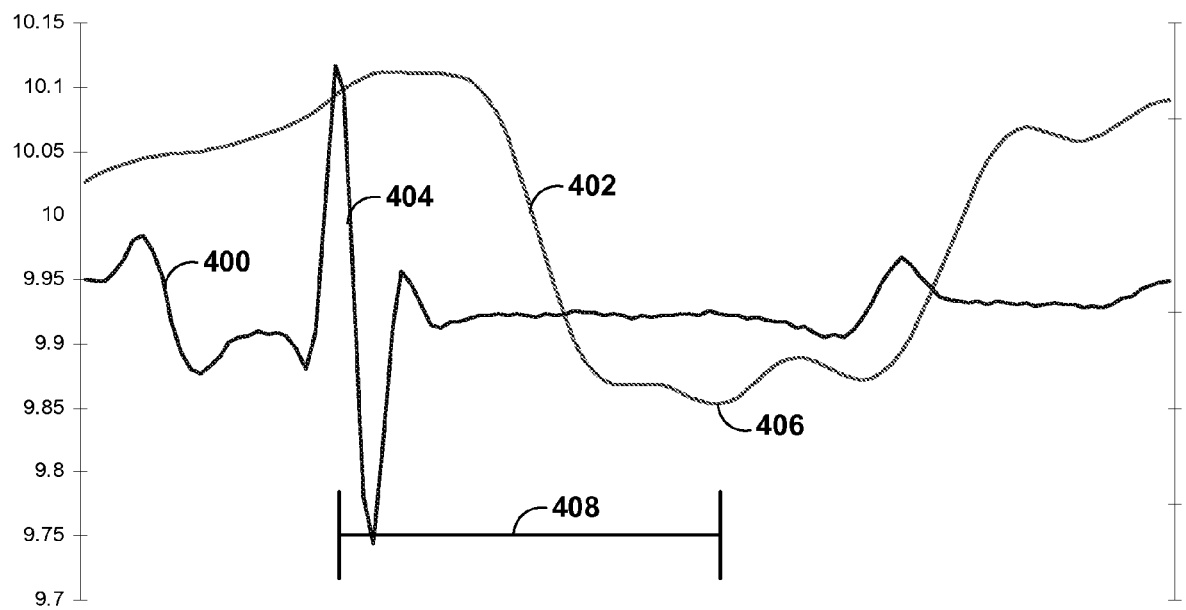
FIG. 25 is a graph illustrating experimental data relating to a time interval between a cardiac electrical event and a fiducial point of an impedance waveform.

FIG. 25 is a graph illustrating experimental data relating to a time interval between a cardiac electrical event within electrogram 400 and a fiducial point of impedance waveform 402. In particular, the graph of FIG. 24 depicts measurement of time interval 408 from R-wave 404 to minimum 406 of impedance waveform 402. Time interval 408 may be a potential indicator of change in afterload associated with a disease such as hypertension.

Figure 26:
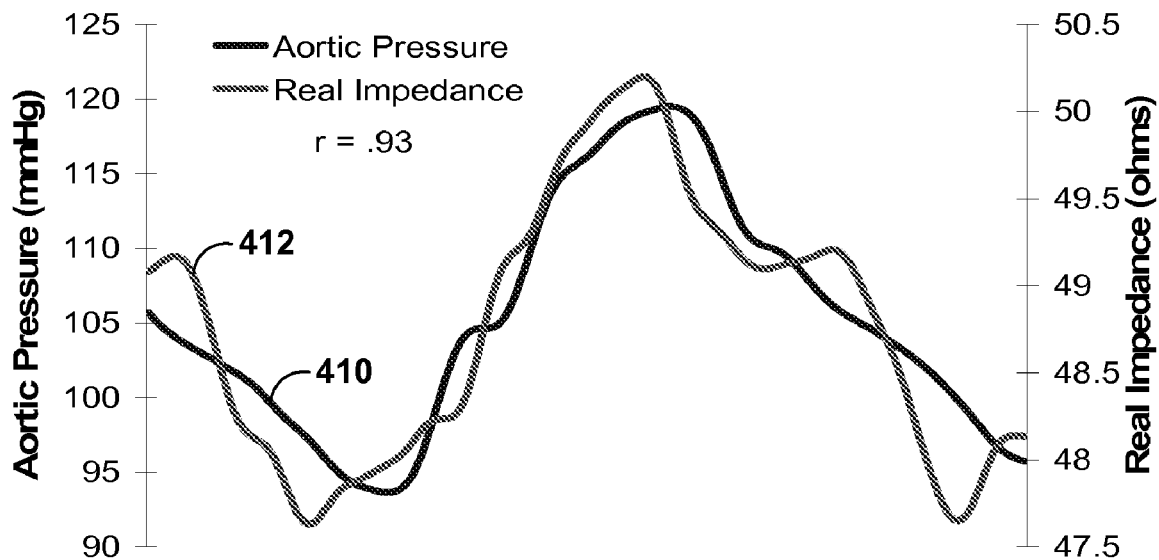
FIG. 26 is a graph illustrating experimental data relating to aortic pressure and impedance waveform morphologies measured in another anesthetized porcine over one cardiac cycle during expiration.
Figure 27:
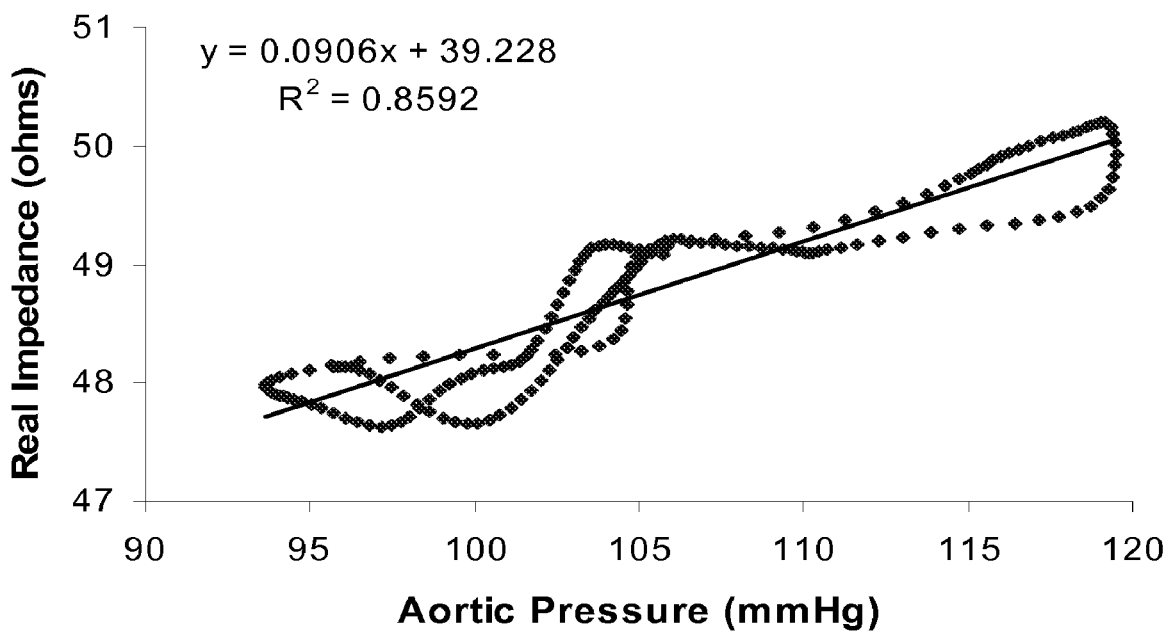
FIG. 27 is a graph that depicts a linear regression plot of the data shown in FIG. 26.

FIG. 26 is a graph illustrating aortic pressure 410 and impedance 412 waveform morphologies measured in another anesthetized porcine over one cardiac cycle during expiration. A bipolar electrode array (RVcoil-to-Can Emulator) and complex impedance circuit (4 kHz stimulation frequency@8.5 µA) was used to measure cardiac impedance. A Millar catheter, positioned in the ascending aorta was used to measure aortic pressure. The aortic pressure waveform and the corresponding real component of complex impedance waveform have a strong correlation (r=0.93). FIG. 27 depicts a linear regression plot of the data shown in FIG. 26.

Figure 28:
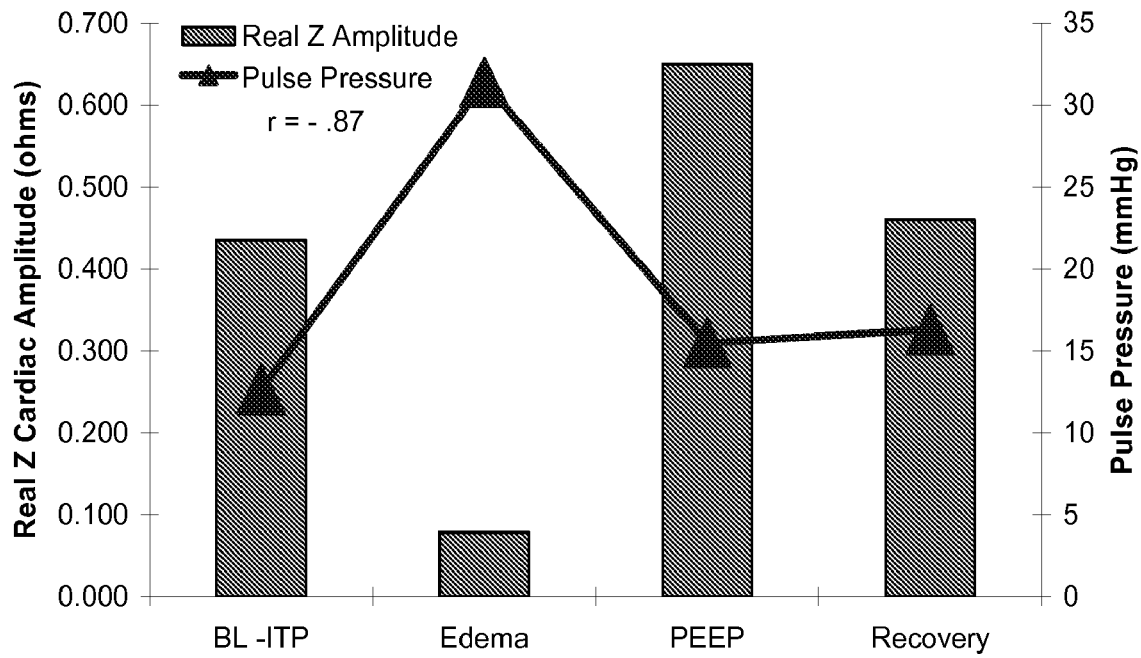
FIG. 28 is a graph illustrating experimental data relating to pulse pressure and a measured impedance.

FIG. 28 is a graph illustrating experimental data relating to pulse pressure and a measured impedance. FIG. 28 depicts a negative correlation (r=−0.87) during an acute model of pulmonary edema comparing pulse pressure to real impedance amplitude in nine animals. In this study, pulmonary edema was confirmed in 3.36±1.14 hours which is the time from baseline with negative intratracheal pressure (−ITP) applied at −30 mmHg to edema confirmation (Edema). The increase in pulse pressure and decrease in real impedance amplitude during edema confirmation is most likely due to the administration of constant rate infusion of phenylephrine (vasoconstrictor) and accumulation of pulmonary fluid and/or atelectasis respectively. Vasoconstrictive drugs increase afterload and increase pulse pressure. Pulmonary fluid and/or atelectasis cause a decrease in real impedance which therefore cause the amplitude of the real impedance cardiac component to decrease since the left lung is anatomically and in the electrical analog, parallel to the aorta. The subsequent decrease in pulse pressure after 1 hour of Positive End Expiratory Pressure (PEEP) set at 5 cm $H_2O$, is most likely due to the termination of the vasoconstrictive drug whereas the increase in real impedance magnitude during this intervention is most likely due to pulmonary fluid evacuation via the lymphatic system and/or patent alveoli. The additional one-hour recovery period produced a minimal increase in pulse pressure whereas real impedance magnitude decreased toward baseline. The data of FIG. 28 suggest that the real impedance magnitude may have a negative correlation with pulse pressure in patients with pulmonary edema secondary to heart failure.

Figure 29:
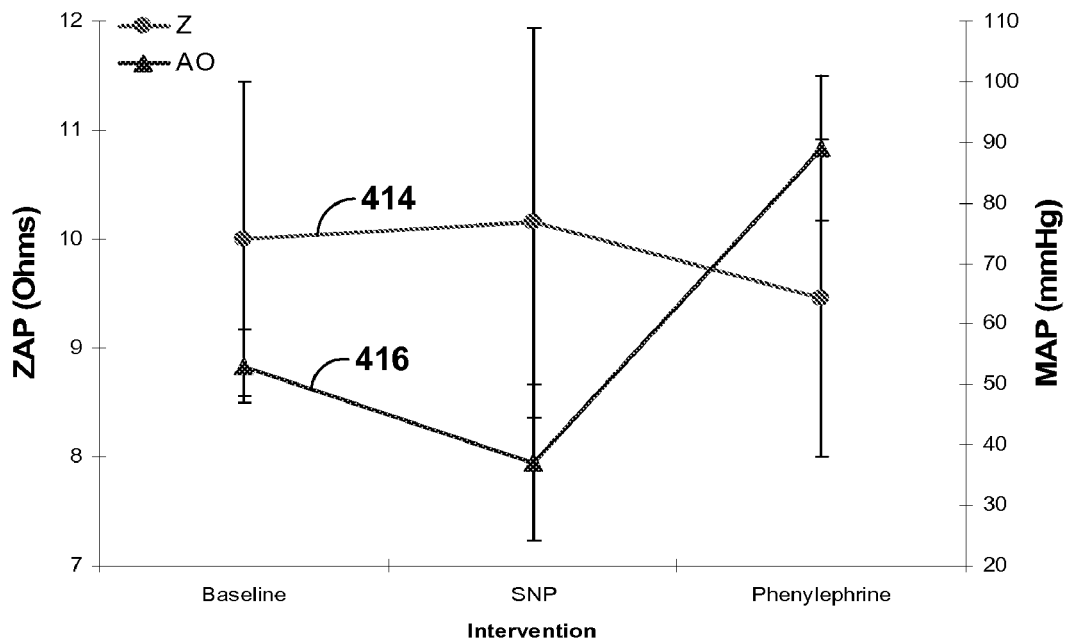
FIG. 29 is a graph illustrating experimental data relating to a calculation of mean arterial pressure from measured impedance and from measured aortic pressure.

FIG. 29 is a graph illustrating experimental data relating to a calculation of mean arterial pressure from measured impedance and from measured aortic pressure. FIG. 29 depicts mean arterial pressure (MAP) 416 and mean impedance (ZAP) 414. Aortic pressure was measured in the aortic arch. Impedance was measured using a quadrapolar electrode configuration in the aortic arch. The graph of FIG. 29 indicates that there is a strong inverse correlation (R=−0.995) comparing impedance to aortic pressure at baseline, sodium nitroprusside (SNP) and phenylephrine constant rate infusion interventions. MAP is calculated as follows based on the aortic pressure waveform:

$$MAP = AO_{DIASTOLE} + 1/3(AO_{SYSTOLE} - AO_{DIASTOLE})$$

In a similar manner, ZAP is calculated as follows based on the impedance waveform:

$$ZAP = Z_{MINIMUM} + 1/3(Z_{MAXIMUM} - Z_{MINIMUM})$$

Sodium nitroprusside is a vasoactive drug that induces peripheral vasodilation. Phenylephrine is a vasoactive drug that induces peripheral vasoconstriction. With this model, cardiac function is not impaired and pump function is maintained while afterload is modified. Compared to baseline, after SNP was administered and maintained, MAP decreased whereas ZAP increased. This phenomenon supports the theory that if a patient is hypotensive due to decreased afterload, MAP is lower and more blood volume exits the major arteries and impedance measured increases. Conversely, after phenylephrine was administered and maintained, MAP increased whereas ZAP decreased. This phenomenon supports the theory that if a patient is hypertensive, MAP is higher and more blood volume resides in the major arteries rather than in the peripheral vasculature.

Figure 30:
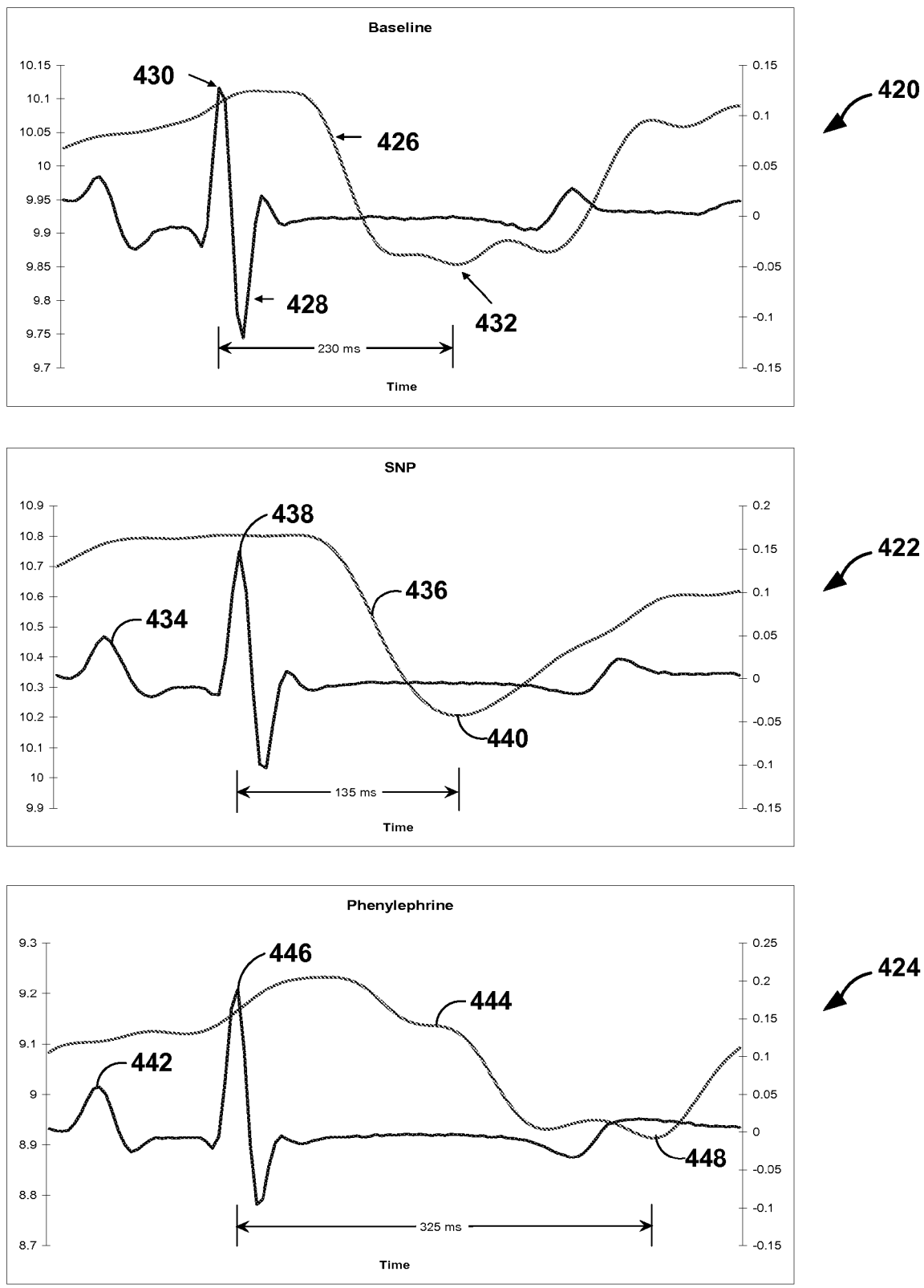
FIG. 30 includes three graphs that illustrate experimental data for various treatments and resulting time intervals between cardiac electrical events and fiducial points on impedance waveforms.

FIG. 30 includes three graphs 420, 422, 424 that illustrate experimental data for various treatments and resulting time intervals between cardiac electrical events and fiducial points on impedance waveforms. Graphs of FIG. 30 depict ECG 428, 434, 442 and Impedance 426, 436, 444 data acquired from a quadrapolar electrode configuration in the aortic arch at baseline (graph 420), sodium nitroprusside (graph 422) and phenylephrine (graph 424) constant rate infusions. As the animal becomes more vasoreactive, the time constant from R-wave sense 430, 438, 446 to Z-wave minimum 432, 440, 448 changes. This data support the notion that ECG and Z data may be used as a surrogate to pressure for monitoring afterload.

Figure 31:
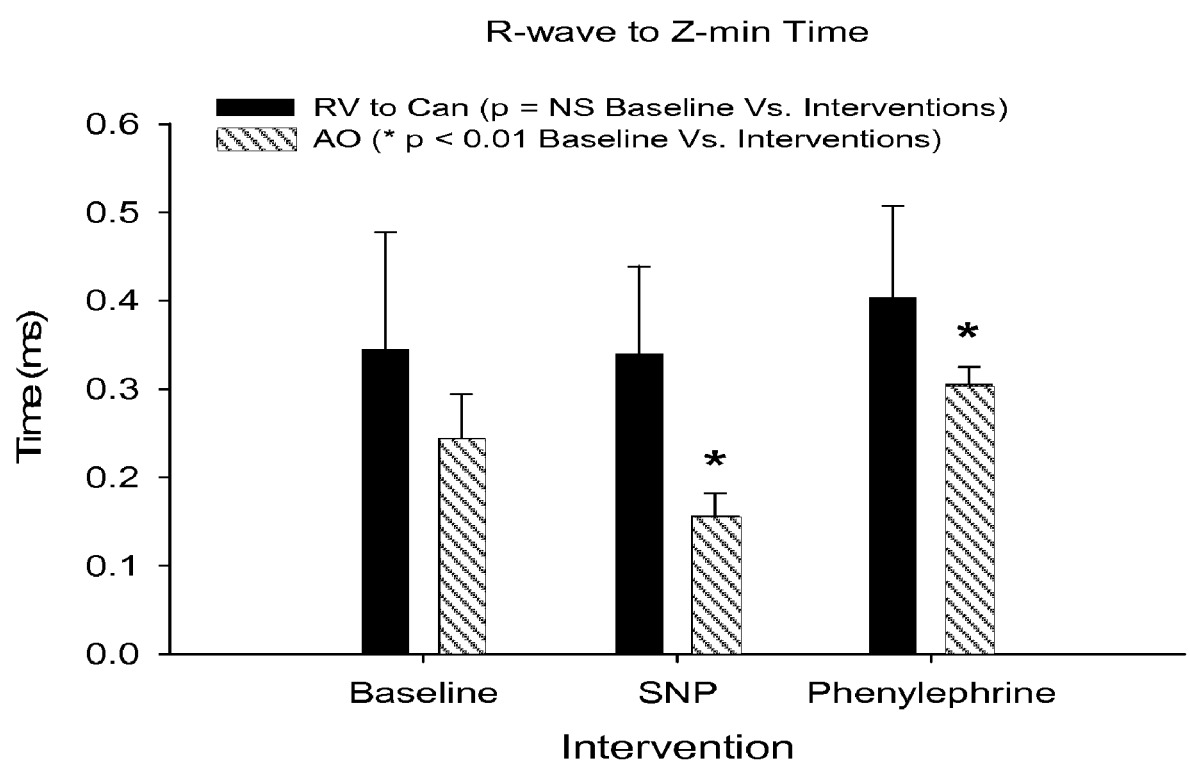
FIG. 31 is a graph illustrating experimental data relating to a comparison of a tripolar electrode configuration between the right ventricle and can emulator and a quadrapolar electrode configuration in the aortic arch in six animals.

FIG. 31 is a graph illustrating experimental data relating to a comparison of a tripolar electrode configuration between the right ventricle and can emulator (RV-CAN, solid bars) and a quadrupolar electrode configuration in the aortic arch (AO, hashed bars) in six animals (n=6). Although the trend is the same in both electrode configurations, electrodes within or that potentially transect the aorta show a significant difference (p<0.01) post afterload modifying drug interventions.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described herein may also be embodied in a computer readable medium containing instructions. Instructions embedded in a computer readable medium may cause a programmable processor, or other processor, to perform the method, e.g. when the instructions are executed. A computer readable medium may be a computer readable storage medium. Computer readable storage media may include, for example, random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

The invention claimed is:

1. A method comprising:
   measuring a plurality of impedance values of a path within a patient over time, wherein the path includes at least one blood vessel or cardiac chamber of the patient, and wherein the impedance values vary as a function of blood pressure within the at least one vessel or chamber;
   determining a plurality of values of an impedance parameter over time based on the measured impedance values, wherein each of the impedance parameter values is determined based on a respective sub-plurality of the impedance values, determining the plurality of values of the impedance parameter comprising
   identifying an R-wave for a current cardiac cycle,
   identifying a maximum impedance and a minimum impedance for the current cardiac cycle,
   determining a first time interval between the R-wave and the minimum impedance,
   determining a second time interval between the R-wave and the maximum impedance, and
   determining a ratio of the first time interval and the second time interval;
   comparing the ratio of the current cardiac cycle to a ratio of a prior cardiac cycle; and
   identifying a change in a cardiovascular parameter related to the blood pressure based on the comparison.

2. The method of claim 1, further comprising triggering an alert in response to the change in the cardiovascular parameter.

3. The method of claim 1, further comprising modifying a therapy delivered to the patient in response to the change in the cardiovascular parameter.

4. The method of claim 1, wherein determining a plurality of values of an impedance parameter further comprises identifying a fiducial point of the plurality of impedance values for the current cardiac cycle, and determining a third time interval between the R-wave and the fiducial point, and
   comparing the third time interval for the current cardiac cycle to a third time interval for a previous cardiac cycle.

5. A non-transitory computer-readable medium comprising instructions for causing a programmable processor to:
   measure a plurality of impedance values of a path within a patient over time, wherein the path includes at least one blood vessel or cardiac chamber of the patient, and wherein the impedance values vary as a function of blood pressure within the at least one vessel or chamber;
   determine a plurality of values of an impedance parameter over time based on the measured impedance values, wherein each of the impedance parameter values is determined based on a respective sub-plurality of the impedance values, wherein the instructions for causing the programmable processor to determine the plurality of values of the impedance parameter comprise instructions that cause the programmable processor to:
   identify an R-wave for a current cardiac cycle,
   identify a minimum impedance and a maximum impedance for the current cardiac cycle,
   determine a first time interval between the R-wave and the minimum impedance,
   determine a second time interval between the R-wave and the maximum impedance, and
   determine a ratio of the first time interval and the second time interval;
   compare the ratio of the current cardiac cycle to a ratio of a prior cardiac cycle;
   identify a change in a cardiovascular parameter related to the blood pressure based on the comparison; and
   execute a programmed response upon identifying a change in the cardiovascular parameter.

* * * * *